United States Patent
Siciliano et al.

(10) Patent No.: US 12,411,123 B2
(45) Date of Patent: Sep. 9, 2025

(54) METHODS AND SYSTEMS FOR STIMULATING AND DETECTING THE BIOLOGICAL DEGRADATION OF HYDROCARBONS AND BIOGEOCHEMICAL CYCLES IN CONTAMINATED SOILS

(71) Applicant: Environmental Material Science Inc., Edmonton (CA)

(72) Inventors: Steven Douglas Siciliano, Saskatoon (CA); John Derek Peak, Saskatoon (CA); Paolo Giuseppe Mussone, Edmonton (CA); Curtis Senger, Edmonton (CA)

(73) Assignee: Environmental Material Science Inc., Edmonton (CA)

( * ) Notice: Subject to any disclaimer, the term of this patent is extended or adjusted under 35 U.S.C. 154(b) by 357 days.

(21) Appl. No.: 17/230,869

(22) Filed: Apr. 14, 2021

(65) Prior Publication Data
US 2021/0356450 A1    Nov. 18, 2021

(30) Foreign Application Priority Data

Nov. 5, 2020   (CA) .................................. 3098187

(51) Int. Cl.
*G01N 33/24*    (2006.01)
(52) U.S. Cl.
CPC .................... *G01N 33/241* (2013.01)
(58) Field of Classification Search
CPC .............................. G01N 33/241; G01N 27/70
See application file for complete search history.

(56) References Cited

U.S. PATENT DOCUMENTS

| 5,120,160 A | 6/1992 | Schwengel |
| 5,228,804 A | 7/1993 | Balch |

(Continued)

FOREIGN PATENT DOCUMENTS

| CA | 2301308 A1 | 9/2001 | |
| CA | 2501530 | * 1/2005 | ............... G01F 1/00 |

(Continued)

OTHER PUBLICATIONS

"Petroleum Hydrocarbon Remediation by In-situ Chemical Oxidation at Colorado Sites" Department of Labor and Employment Division of Oil and Public Safety, pp. 1-22; Jun. 14, 2007 (Year: 2007).*

(Continued)

*Primary Examiner* — Michael J Dalbo
*Assistant Examiner* — Kaleria Knox
(74) *Attorney, Agent, or Firm* — Robert A. Nissen

(57) ABSTRACT

This document discusses depletion sensors and soil monitoring systems, including soil bioremediation systems and methods. A depletion sensor may have a sensor tubing; and a plurality of sensor modules on or within the sensor tubing and longitudinally spaced in series along the sensor tubing at different respective longitudinal positions, which correspond to different respective depths of each sensor module when the depletion sensor is in use inserted within underground soil below a ground surface, each sensor module having: a housing; a sensing part within the housing; and a port in the housing putting the sensing part in fluid communication with an exterior of the sensor tubing at the respective longitudinal position of the sensor module along the sensor tubing. Underground soil monitoring systems may include a network of depletion sensor wells penetrating the ground surface, with each of the depletion sensor wells containing a depletion sensor. Long term in situ biogeo- (Continued)

chemical carbon monitoring of underground soil may be carried out at a site.

15 Claims, 8 Drawing Sheets

(56) References Cited

U.S. PATENT DOCUMENTS

| | | |
|---|---|---|
| 5,279,740 A | 1/1994 | Basile |
| 5,427,944 A | 6/1995 | Lee |
| 5,481,815 A | 1/1996 | Murphy |
| 5,562,588 A | 10/1996 | Higgins |
| 5,570,973 A | 11/1996 | Hunt |
| 5,584,605 A | 12/1996 | Beard |
| 5,609,667 A | 3/1997 | Dickerson |
| 5,611,837 A | 3/1997 | Bossert |
| 5,614,097 A | 3/1997 | Bender |
| 5,658,093 A | 8/1997 | Kawabata |
| 5,681,739 A | 10/1997 | Turick |
| 5,766,929 A | 6/1998 | Orolin |
| 5,833,855 A | 11/1998 | Saunders |
| 5,922,204 A | 7/1999 | Hunter |
| 6,265,205 B1 | 7/2001 | Hitchens |
| 6,268,206 B1 | 7/2001 | Liptak |
| 6,497,534 B1 | 12/2002 | McCoy |
| 6,652,752 B2 | 11/2003 | Ward |
| 6,806,078 B2 | 10/2004 | Newman |
| 6,828,141 B2 | 12/2004 | Kataoka |
| 6,905,288 B2 | 6/2005 | Miyazaki |
| 6,923,596 B2 | 8/2005 | Lessard |
| 6,923,914 B2 | 8/2005 | Perriello |
| 7,175,366 B2 | 2/2007 | Geisel |
| 7,252,986 B2 | 8/2007 | Davis-Hoover |
| 7,263,448 B2 | 8/2007 | Brown |
| 7,384,556 B2 | 6/2008 | Jin |
| 7,441,605 B2 * | 10/2008 | Coronado ............ E21B 17/1035 166/120 |
| 7,645,384 B2 | 1/2010 | Kerfoot |
| 8,277,657 B2 | 10/2012 | Lovley |
| 8,444,962 B2 | 5/2013 | Helmke |
| 8,480,903 B1 | 7/2013 | Taylor |
| 8,950,251 B2 | 2/2015 | Valentine |
| 8,980,619 B2 | 3/2015 | Upreti |
| 9,004,816 B2 | 4/2015 | Reynolds |
| 9,034,633 B2 | 5/2015 | Kumar |
| 9,056,340 B2 | 6/2015 | Fowler |
| 9,399,912 B2 | 7/2016 | McAlary |
| 9,429,452 B2 | 8/2016 | Amiri |
| 9,643,223 B2 | 5/2017 | Smith |
| 10,280,747 B2 * | 5/2019 | AbuAli ................ G01V 9/007 |
| 10,478,652 B2 | 11/2019 | Nzila |
| 10,479,711 B2 | 11/2019 | Noland |
| 10,493,418 B2 | 12/2019 | Yang et al. |
| 10,501,351 B2 | 12/2019 | Angel |
| 10,583,472 B2 | 3/2020 | Noland |
| 10,596,606 B2 | 3/2020 | Zhang |
| 10,737,959 B2 | 8/2020 | Noland |
| 10,882,770 B2 | 1/2021 | Graves |
| 10,883,150 B2 | 1/2021 | Yeber Ortiz |
| 10,927,621 B2 | 2/2021 | Gibson |
| 2003/0059926 A1 | 3/2003 | Detorres |
| 2004/0229342 A1 | 11/2004 | Lunde |
| 2005/0119353 A1 | 6/2005 | Detorres |
| 2005/0221468 A1 | 10/2005 | MacKrell |
| 2006/0046297 A1 * | 3/2006 | Ball ...................... G01N 33/24 436/28 |
| 2009/0252620 A1 | 10/2009 | Lazzara |
| 2010/0216219 A1 | 8/2010 | Hendrickson et al. |
| 2011/0207204 A1 | 8/2011 | Davis |
| 2012/0100598 A1 | 4/2012 | Sinko |
| 2012/0272878 A1 | 11/2012 | Grant |
| 2013/0256220 A1 | 10/2013 | Barker |
| 2013/0288341 A1 | 10/2013 | Paikray |
| 2013/0295650 A1 | 11/2013 | O'Driscoll |
| 2015/0123670 A1 * | 5/2015 | Robbat, Jr. ............ G01N 27/70 324/464 |
| 2015/0231674 A1 | 8/2015 | Ellis |
| 2015/0352610 A1 | 12/2015 | Carpenter |
| 2016/0258922 A1 * | 9/2016 | Formolo ................ E21B 49/00 |
| 2017/0115265 A1 | 4/2017 | Conder |
| 2020/0038926 A1 | 2/2020 | Freim |
| 2020/0363359 A1 * | 11/2020 | Sale ................... G01N 25/4853 |
| 2021/0140908 A1 * | 5/2021 | Van Houweling ..... G01N 33/24 |

FOREIGN PATENT DOCUMENTS

| | | | |
|---|---|---|---|
| CA | 2435064 | | 7/2005 |
| CA | 2768019 | | 8/2013 |
| CN | 103484127 A | | 1/2014 |
| CN | 105032923 A | | 11/2015 |
| CN | 106315868 A | | 1/2017 |
| CN | 106734187 A | | 5/2017 |
| CN | 107470334 A | | 12/2017 |
| CN | 109158417 A | | 1/2019 |
| CN | 109382402 A | | 2/2019 |
| CN | 21089424 U | * | 6/2020 |
| DE | 4240024 A1 | | 6/1994 |
| DE | 102017008700 A1 | | 3/2019 |
| EP | 2217391 B1 | | 12/2008 |
| EP | 2390234 A1 | | 11/2011 |
| EP | 3336303 A2 | * | 6/2018 ............ E21B 34/04 |
| KR | 20090008844 A | | 1/2009 |
| KR | 20090008844 B1 | * | 11/2009 |
| WO | 2017178692 A1 | | 10/2017 |
| WO | WO-2018211366 A1 | * | 11/2018 ........... G06F 18/214 |

OTHER PUBLICATIONS

Wave Control Systems Ltd., Usc-c, Brochure, available Jan. 2020, 2 pages.

Bulmer et al., Effects of Citrate on the Rates and the Mechanisms of Phosphate Adsorption and the Desorption on a Calcareous Soil, Soil Science Society of America Journal, published Mar. 8, 2019, 7 pages, 83(2), DOI=10.2136/sssaj2018.09.0323.

Bulmer et al., Extent and Mechanism of Interaction between Phosphate and Citrate in Calcareous Soil, Soil Science Society of America Journal, published Feb. 8, 2018, 8 pages, 82(2), DOI=10.2136/sssaj2017.08.0289.

Chen et al., Citrate Addition Increased Phosphorus Bioavailability and Enhanced Gasoline Bioremediation, Journal of Environmental Quality, published Aug. 10, 2017, 9 pages, 46(5), DOI=10.2134/jeq2017.02.0064.

Huang et al., Assessing Space, Time, and Remediation Contribution to Soil Pollutant Variation near the Detection Limit Using Hurdle Models to Account for a Large Proportion of Nondetectable Results, Environmental Science and Technology, published May 9, 2019, 10 pages, 53(12), DOI=10.1021/acs.est.8b07110.

Siciliano et al., Total Phosphate Influences the Rate of Hydrocarbon Degradation but Phosphate Mineralogy Shapes Microbial Community Composition in Cold-Region Calcareous Soils, Environmental Science and Technology, published Apr. 15, 2016, 10 pages, 50(10), DOI=10.1021/acs.est.5b05911.

Hamilton et al., Chemical speciation and fate of tripolyphosphate after application to a calcareous soil, Geochemical Transactions, published Jan. 8, 2018, 11 pages, 19(1), DOI=10.1186/s12932-017-0046-z.

Patent Cooperation Treaty, International Search Report, mailed Jan. 25, 2021, 3 pages.

Cooperative Research Centre for Contamination Assessment and Remediation of the Environment, Technical Report No. 44, Technical measurement guidance for LNAPL natural source zone depletion, Aug. 2018, 254 pages.

* cited by examiner

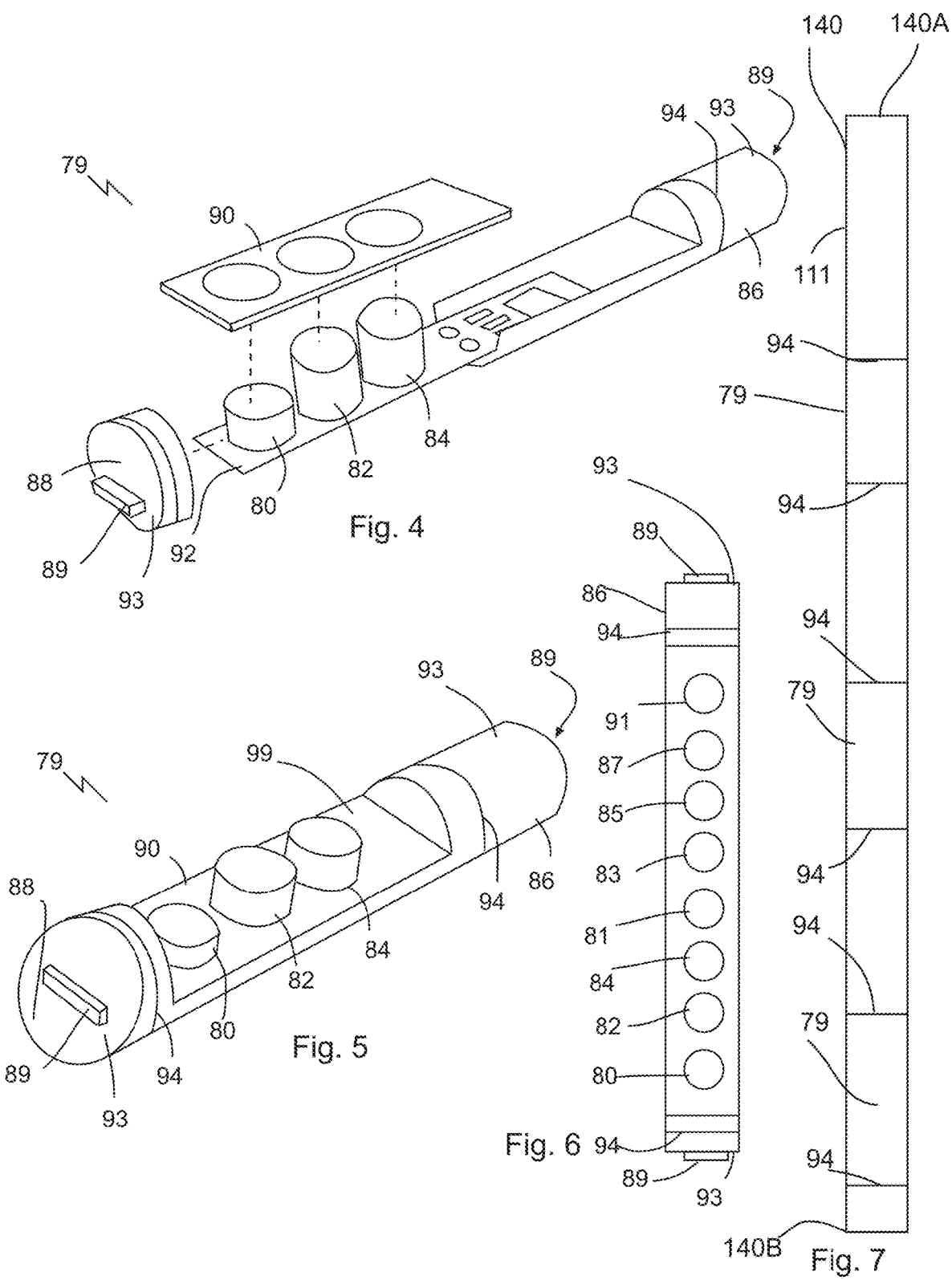

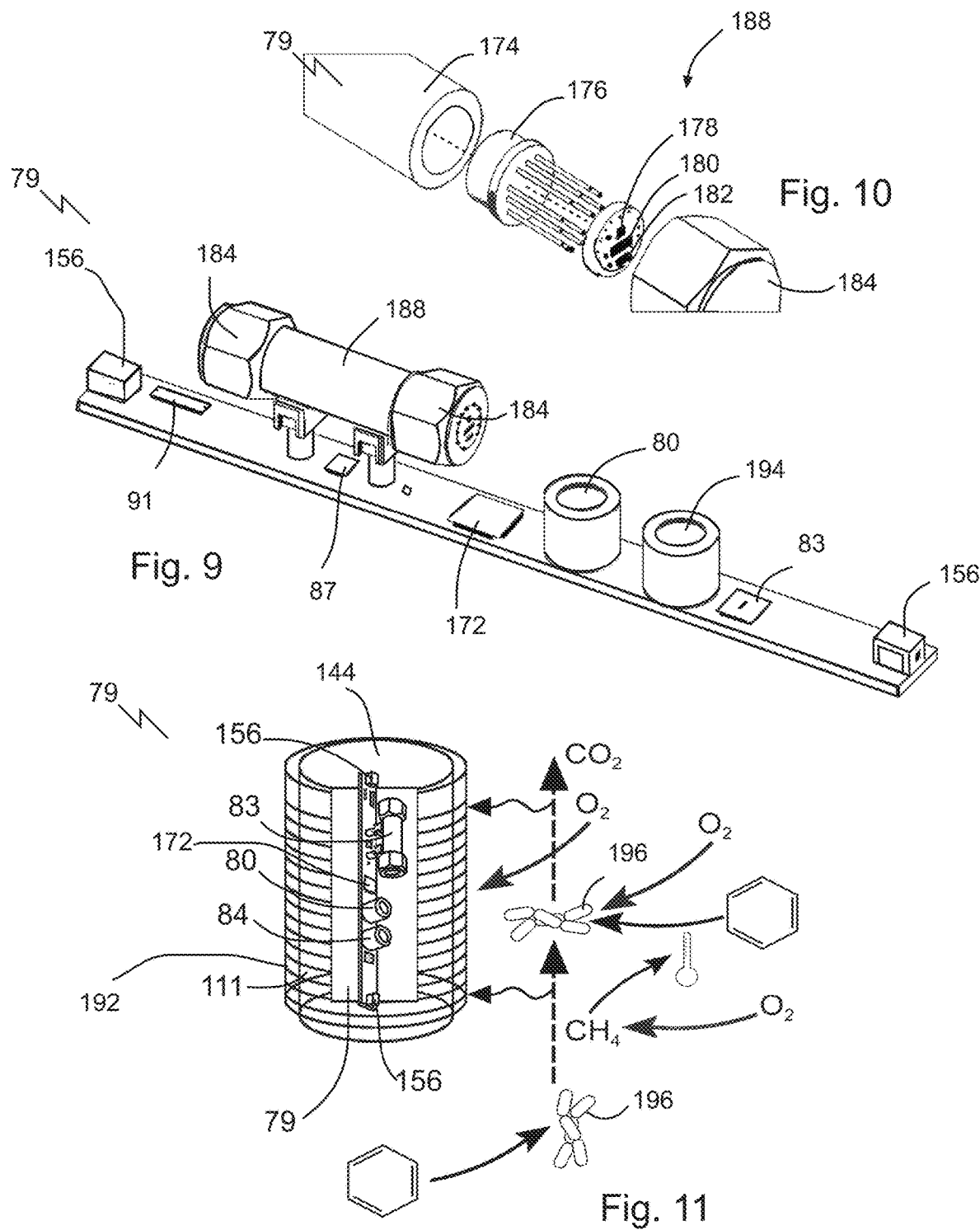

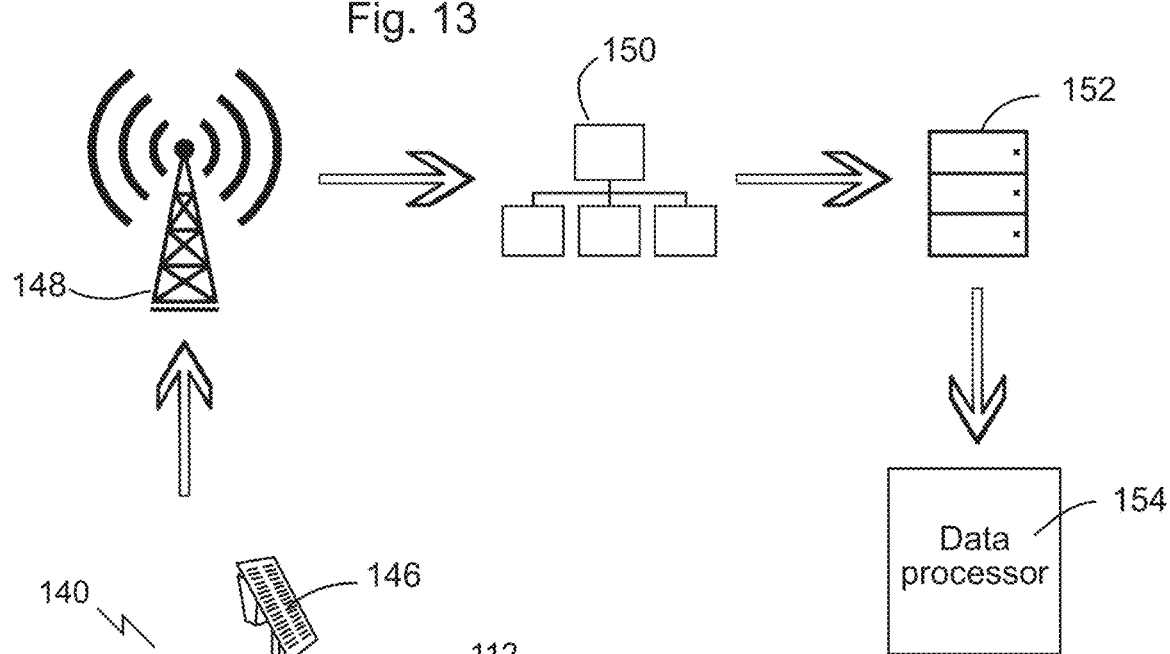
Fig. 13
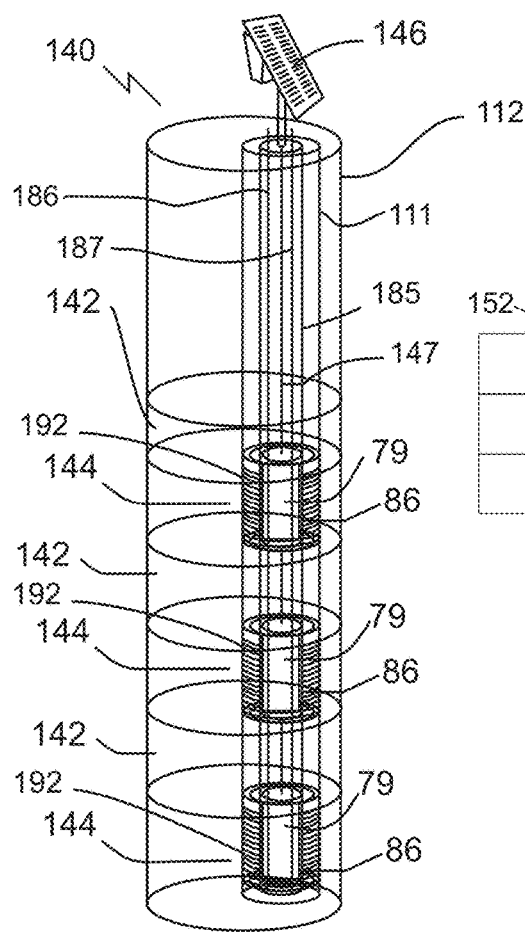
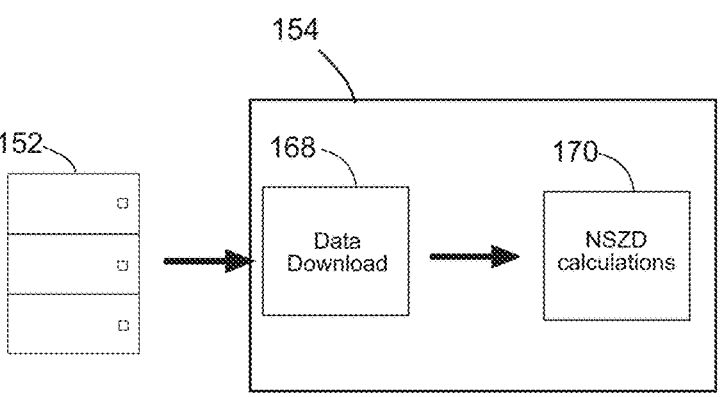
Fig. 14

METHODS AND SYSTEMS FOR STIMULATING AND DETECTING THE BIOLOGICAL DEGRADATION OF HYDROCARBONS AND BIOGEOCHEMICAL CYCLES IN CONTAMINATED SOILS

TECHNICAL FIELD

This document relates to depletion sensors for underground soil, systems for monitoring and/or stimulating the biological degradation of hydrocarbons in contaminated soils, and related methods.

BACKGROUND

The following paragraphs are not an admission that anything discussed in them is prior art or part of the knowledge of persons skilled in the art.

Bioremediation involves the use of biological processes to degrade and remove contaminants from the environment. The process of bioremediation uses microorganisms to convert chemical compounds, such as gasoline, into energy, cell mass and biological waste products. Typically, the remediation process is carried out in one of two ways: (1) the soil is removed, then treated or (2) the remediation process is carried out in situ.

SUMMARY

A depletion sensor is disclosed comprising: a sensor tubing; and a plurality of sensor modules on or within the sensor tubing and longitudinally spaced in series along the sensor tubing at different respective longitudinal positions, which correspond to different respective depths of each sensor module when the depletion sensor is in use inserted within underground soil below a ground surface, each sensor module having: a housing; a sensing part within the housing; and a port in the housing putting the sensing part in fluid communication with an exterior of the sensor tubing at the respective longitudinal position of the sensor module along the sensor tubing.

An underground soil monitoring system is disclosed comprising a network of depletion sensor wells penetrating the ground surface, with each of the depletion sensor wells containing a depletion sensor.

A method is disclosed of long term in situ biogeochemical carbon monitoring of underground soil at a site, the method comprising monitoring, over an extended period, levels of carbon-containing compounds in the underground soil, using one or more depletion sensor wells that are arranged within the underground soil below a ground surface at the site and that remain in the underground soil over the extended period, each of the one or more depletion sensor wells having a plurality of sensors located at one or more isolated depth zones along the depletion sensor well.

An underground soil monitoring system is disclosed comprising: one or more depletion sensor wells, the one or more depletion sensor wells penetrating hydrocarbon contaminated soil below a ground surface at an impacted site, each of the one or more depletion sensor wells containing: a sensor tubing; and a plurality of sensor modules on or within the sensor tubing and longitudinally spaced in series along the sensor tubing at different respective depths in the depletion sensor well; and a controller connected to receive sensor data from the one or more depletion sensor wells and to one or both store and transmit the data.

In some cases a method of in situ treatment of hydrocarbon contaminated soil at an impacted site is disclosed, the method comprising: injecting liquid chemicals in situ through a plurality of injection wells into the hydrocarbon contaminated soil, which is located below a ground surface at the impacted site, in which the liquid chemicals are selected to biostimulate a microbial degradation process of hydrocarbons to remediate the impacted site, in which the injection of liquid chemicals is controlled by a controller; and monitoring the microbial degradation process using a plurality of sensor wells, which are located within the hydrocarbon contaminated soil.

In some cases a hydrocarbon contaminated soil remediation system is disclosed comprising: one or more liquid chemical reservoirs; an injector connected to the one or more liquid chemical reservoirs; a network of injection wells connected to the injector, the plurality of injection wells penetrating hydrocarbon contaminated soil below a ground surface at an impacted site; a network of hydrocarbon depletion sensor wells, arranged within the network of injection wells, the hydrocarbon depletion sensor wells penetrating the ground surface at the impacted site, for example penetrating or adjacent to hydrocarbon contaminated soil below the ground surface at the impacted site; and a controller connected to receive sensor data from the hydrocarbon depletion sensor wells and to control the injector to dispense liquid chemicals into the hydrocarbon contaminated soil via the injection wells, in which the liquid chemicals are selected to biostimulate a microbial degradation process of hydrocarbons to remediate the impacted site.

This document discusses systems and methods of using naturally occurring and/or resident bacteria in soil remediation. A chemical solution is added to the soil comprising one or more of the following chemicals: nitric acid, ferric ammonium citrate, sodium triphosphate and magnesium sulfate. Phosphorus bioavailability may limit the biodegradation of gasoline in calcareous soils. The addition of citrate may increase hydrocarbon degradation and stimulate anaerobic microbial activity, and increase the bioavailability of phosphorus. By increasing citrate concentrations in the soil, the amount of adsorbed phosphorus decreases allowing for increased transport of phosphorus. In some cases the injection of such chemicals into the soil stimulates microbial activity to degrade hydrocarbons and remediate the soil.

In some cases the solution is initially separated into two tanks, for example one containing both the nitric acid and ferric ammonium citrate, and the other containing sodium triphosphate and magnesium sulfate. The chemicals may be separated initially to prevent precipitation that may occur when the chemicals are mixed into a single solution.

The chemicals may be released from their respective tanks and directed through a strainer to remove any precipitated solids that may have formed in the tank, which may occur when the concentrations of the chemicals are incorrect. The solution may pass through an uninterruptible control system (UCS). The solutions may reach a pump, though if there is enough head pressure, the solution may go through the entire distribution system without the use of the pumps. The solutions may be mixed together with either groundwater extracted through the use of a submersible pump or a back-up water tank. The solution may pass through another strainer and through a gear pump to various injection galleries. USC control valves may adjust flow to an individual gallery if necessary.

The method may include injecting a combination of amendments using a unique injection system called AC-Medusa (Adaptively Controlled-Mobile Environmental Deployment Unit Stimulating Attenuation). AC-Medusa may be a solar powered injection system that uses on site groundwater or any suitable source of water to simultaneously stimulate and track hydrocarbon depletion. AC-Medusa may slowly feed across multiple injection points a solution that stimulates the biodegradation of hydrocarbons in contaminated soils over time. AC-Medusa may use low concentrations and low flows to avoid eutrophying the site, causing hydrological short-circuiting, or injection point fouling. AC-Medusa may protect from overshooting with nitrogen and unintentionally creating a nitrate plume.

AC-Medusa may incorporate an Uninterruptible Chemical Supply (UCS) system for precise mixing and delivery of amendments onsite. The use of a UCS system for mixing control may allow the AC-Medusa to use on site groundwater as the carrier of the mixing solution. Multiple UCS systems may ensure that injection volumes across multiple injection wings (arrays of linked points) do not cause hydrological short circuiting due to over-pressure as well as insuring that injection points do not run dry and thereby foul.

AC-Medusa may be designed to not only accelerate natural source zone depletion (NSZD) processes, but may also provide site owners with continuous estimate of ongoing NSZD. Site owners may use this information to continuously update predictions of when the site may reach closure. AC-Medusa may provide estimates of NSZD by incorporating information from depletion stations. The depletion stations may be soil sensors installed at least three different depths, surrounded by a clean sand pack, and sealed from the surface with bentonite. The soil sensors may include non-dispersive infrared sensors and/or ultra-violet sensors to continuously estimate carbon dioxide, methane, oxygen, temperature and relative humidity within the soil profile. Each depletion station may be solar powered and communicate the data directly with a UCS within AC-Medusa. The AC-Medusa may send this information, for example via cellular service, to a central database. Based on the depth profiles of soil gas and temperature, a user or computer may then estimate hydrocarbon loss in the subsurface as a result of the AC-Medusa injection activity.

Hydrocarbon loss may be estimated based on a site-specific calibration model of NSZD. Stimulant Enhancement studies of selected impacted soil cores from a site may be carried out to confirm that the injection program is effective in the impacted areas. During Stimulant Enhancement studies, the user may monitor hydrocarbon loss as well as carbon dioxide, methane, oxygen, temperature and relative humidity in the soil. The user may then use machine learning to build a predictive model for the site at which AC-Medusa is installed. The machine learning algorithm may be based on established guidance estimates as well as site specific values. Hydrocarbon loss may be visualized across the entire site using spatial interpolation. A user may then use this information to alter UCS behavior in AC-Medusa to modify stimulant injection concentrations and volumes across the site in a spatially targeted manner. The NSZD estimates may allow the AC-Medusa to use adaptive feedback to maximize hydrocarbon degradation on site.

AC-Medusa may reduce carbon liability from 8.2 t $CO_2$-equivalents m-3 soil to between 0.0003 and 1.3 t $CO_2$-equivalents m-3 soil. The systems and methods may deliver site-specific remedial objectives at costs significantly lower than traditional technologies and may increase remediation rates by up to 500%, reducing time to completion by up to 83% when compared to traditional technologies. AC-Medusa may be designed to accelerate natural depletion processes and also provide site owners with a definitive estimate of ongoing depletion allowing continuously updated predictions of when the site may reach closure. AC-Medusa may provide site owners the ability to remotely track hydrocarbon depletion and spatially adapt the injection system to maximize hydrocarbon depletion.

In some cases the systems and methods provide for one or more of:
a. The use of low-pressure UCS allows for solar powered injection and distribution systems that are resilient to fouling and short-circuiting.
b. The use of on-site groundwater removes the need for routine site access.
c. Stand-alone depletion monitors allow distributed estimates of natural source zone depletion of hydrocarbons.
d. Depletion monitor communication via UCS, allows integrated reporting and control via the AC-Medusa, thereby providing remote access and control of the remediation system.
e. Site-specific calibration allows site owners to estimate current hydrocarbon depletion without visiting the site, and thereby extrapolate time to closure.
f. UCS distribution to different injection wings, allows remote control of amendment solution concentration and volume.

In various embodiments, there may be included any one or more of the following features: Bore wall sealing parts are on the exterior of the sensor tubing longitudinally separating adjacent sensor modules. The one or more bore wall sealing parts comprise a gasket circumferentially extending around the sensor tubing. Each sensor module comprises one or more of an oxygen sensor, a carbon dioxide sensor, a methane sensor, a hydrocarbon sensor, a temperature sensor, an electrical conductivity sensor, and a humidity sensor. Additional sensors may include sensors to detect sulfur hexafluoride and/or nitrous oxide. Each sensor module comprises the oxygen sensor, the carbon dioxide sensor, and the hydrocarbon sensor, as well as additional sensors. The plurality of sensor modules comprises three or more sensor modules. The sensor modules are formed within the sensor tubing. For each sensor module, the housing is defined as a portion of the sensor tubing that is indented or cut out to define a receptacle within which is positioned the respective sensing part. Each sensor module further comprises a fluid permeable filter between the sensing part and the port. The fluid impermeable pack comprises a bentonite pack. An above-ground solar power source is connected to power the sensor modules. A controller is connected to one or both store and receive data from, the sensor modules. The controller comprises a transmitter for transmitting data from the sensor modules to a remote location. The underground soil may be hydrocarbon contaminated soil, and the controller is connected to control the injection of liquid chemicals in situ through a plurality of injection wells into the hydrocarbon contaminated soil, in which the liquid chemicals are selected to biostimulate a microbial degradation process of hydrocarbons to remediate the impacted site. The embodiments may be used in applications outside of hydrocarbon impacts, for example to detect carbon sequestration and/or the impacts of soil management such as in agricultural or forestry activities. The plurality of sensor modules are configured to monitor a microbial degradation process of hydrocarbons in the underground soil. The plurality of sensors take continuous or periodic readings over the extended period. The extended period is a month or longer. The extended period is a year or longer. Each depletion sensor well contains a sensor tubing; the plurality of sensors on each depletion sensor well are a plurality of sensor modules on or within the sensor tubing and longitudinally spaced in series along the sensor tubing at different respective longitudinal positions, which correspond to different respective depths of each sensor module below the ground surface. Each sensor module has a housing; a sensing part within the housing; and a port in the housing putting the sensing part in fluid communication with an exterior of the sensor tubing at the respective longitudinal position of the sensor module. A controller is connected to the depletion sensor wells, the controller configured to one or more of: collect the data continuously or at intervals; store the data locally; and transmit the data. The network of depletion sensor wells includes: depletion sensor wells that are inserted into the hydrocarbon contaminated soil; and depletion sensor wells that are inserted into underground soil adjacent to the hydrocarbon contaminated soil. Drilling the network of depletion sensor wells. Each of the plurality of sensor wells comprise one or more of an oxygen sensor, a carbon dioxide sensor, a methane sensor, a hydrocarbon sensor, a temperature sensor, and a humidity sensor. Each of the plurality of sensor wells comprise the oxygen sensor, the carbon dioxide sensor, and the hydrocarbon sensor. Each of the plurality of sensor wells comprise: a sensor tubing located in the sensor well; and a sensor module forming part of the sensor tubing, the sensor module having: a sensing part within the sensor tubing; a port in the sensor tubing in fluid communication with the sensing part; and a fluid permeable filter between the sensing part and the port. Each sensor tubing has a plurality of sensor modules longitudinally spaced along the sensor tubing at different respective depths in the sensor well. The sensor wells are connected to send sensor data to the controller. Injecting liquid chemicals in situ through a plurality of injection wells into the hydrocarbon contaminated soil, in which the liquid chemicals are selected to biostimulate a microbial degradation process of hydrocarbons to remediate the site. Adjusting a flux of liquid chemicals may be performed in response to the sensor data from the plurality of sensor wells. Adjusting with the controller, the injection of the liquid chemicals, which may be modified in response to the sensor data from the plurality of sensors to maintain a rate of the microbial degradation process within a predetermined range. Adjusting further comprises increasing one or more of a concentration of liquid chemicals and a flow rate of the liquid chemicals if one or more of the following situations are detected: a rate of change in oxygen levels are outside of a predetermined range; a rate of change in $CO_2$ levels are outside of a predetermined range; a rate of change in methane levels are outside of a predetermined range; a rate of change of hydrocarbon levels are outside of a predetermined range; a rate of change of temperature levels are outside of a predetermined range; pH levels are outside of a predetermined range; or humidity levels are outside of a predetermined range. Adjusting further comprises decreasing one or more of a concentration of liquid chemicals and a flow rate of the liquid chemicals if one or more of the following situations are detected: a rate of change of oxygen levels are outside of a predetermined range; a rate of change in $CO_2$ levels are outside of a predetermined range; a rate of change in methane levels are outside of a predetermined range; a rate of change in hydrocarbon levels are outside of a predetermined range; a rate of change in temperature levels are outside of a predetermined range; pH levels are below a predetermined range; and humidity levels are outside a predetermined range. Adjusting further comprises one or more of: increasing one or more of a relative proportion and injection rate of water in the liquid chemicals if humidity levels are below a predetermined range; and decreasing one or more of a relative proportion and injection rate of water in the liquid chemicals if humidity levels are above the predetermined range. The predetermined range of temperature is 3-4 degrees above initial ambient soil temperature at or adjacent the impacted site. The predetermined range of pH is between 0 and 3 below initial ambient soil pH at or adjacent the impacted site. The plurality of injection wells comprise a plurality of groups of one or more injection wells each associated with one or more respective adjacent sensor wells; and adjusting with the controller the injection of the liquid chemicals comprises adjusting the injection of liquid chemicals to each group of one or more injection wells based on the sensor data of the one or more respective adjacent sensor wells independent of the injection to the other groups. Injecting further comprising injecting the liquid chemicals with an injector. The injector is structured to maintain predetermined flow rates of liquid chemicals into the plurality of injection wells for months without stopping. The injector comprises one or more dosing stations each having one or more liquid chemical reservoirs. Each dosing station comprises, downstream of the liquid chemical reservoir: a control valve connected to the liquid chemical reservoir; a columnar reservoir connected to the control valve; a pump connected to the columnar reservoir; a dosing station sensor connected to sense level or pressure in the columnar reservoir; and an injection controller connected to the dosing station sensor and connected to operate the pump and control valve to provide a predetermined flow rate of liquid chemical downstream. The injector comprises a mixing station where the liquid chemical concentrates are diluted with dilution water. Supplying the dilution water to the mixing station from a groundwater supply at the impacted site. Pumping the dilution water to surface using a submersible pump. The liquid chemicals comprise nitric acid, ferric ammonium citrate, sodium tripolyphosphate, and magnesium sulfate. A first dosing station has a liquid chemical reservoir comprising nitric acid and ferric ammonium citrate. A second dosing station has a liquid chemical reservoir comprising sodium tripolyphosphate and magnesium sulfate. Injecting further comprises injecting the liquid chemicals at one or more of 1-5 liters per minute and at between 0 and 10 pounds per square inch (psi). Injecting further comprises injecting the liquid chemicals at 0.1-1 mmol/L. The controller comprises a transmitter that wirelessly transmits and receives control signals to and from an off-site central computer. A method includes drilling and installing the plurality of injection wells and the plurality of sensors wells. The hydrocarbon contaminated soil is bounded by and defines a volume of soil under the ground surface at the impacted site, and further comprising determining boundaries of the volume of soil, in which drilling and installing comprises distributing the plurality of injection wells about the volume of soil to permit the injection of the liquid chemicals to saturate the volume of soil. A method includes powering the injecting and monitoring steps may use one or more solar power collectors. The impacted site is a former or current fuel dispensing station, a former or current oil and gas producing well site, a former or current fuel storage facility, a former or current pipeline right of way, or any site with current or previous activities that resulted in the release of hydrocarbons onto a ground surface or into a ground subsurface. The plurality of injection wells are arranged one or more of: 3-4.5 m apart from one another; and 2-3 m below the ground surface. Injecting comprises injecting at below fracturing pressures. A system may be structured to carry out the method or any part thereof. The controller and one or more liquid chemical reservoirs are located in a transport container that is mounted on or forms part of a wheeled trailer or skid. One or more depletion sensor wells comprise a gas delivery tube. One or more depletion sensor wells comprise a water sampling structured to sample groundwater present in the depletion sensor well.

The foregoing summary is not intended to summarize each potential embodiment or every aspect of the subject matter of the present disclosure. These and other aspects of the device and method are set out in the claims.

BRIEF DESCRIPTION OF THE FIGURES

Embodiments will now be described with reference to the figures, in which like reference characters denote like elements, by way of example, and in which:

FIGS. 4 and 5 are exploded and assembled perspective views of a sensor module used in the sensor wells of FIG. 1.

FIG. 6 is a side elevation view of a further embodiment of a sensor module.

FIG. 7 is a side elevation view of a depletion sensor for inserting into a sensor well.

FIG. 9 is a perspective view of a sensor module that may be used in the sensor wells of FIG. 1.

FIG. 10 is an exploded perspective view of a multichannel infrared sensor in FIG. 9.

FIG. 11 is a perspective view of a sensor module along with images that illustrate conceptually the remediation process.

FIG. 13 is a schematic illustrating a process of data collection, transfer and processing of the data collected from the sensor modules of a depletion sensor used in the system of FIG. 12.

FIG. 14 an overview of a data analysis process.

DETAILED DESCRIPTION

Figure 1:
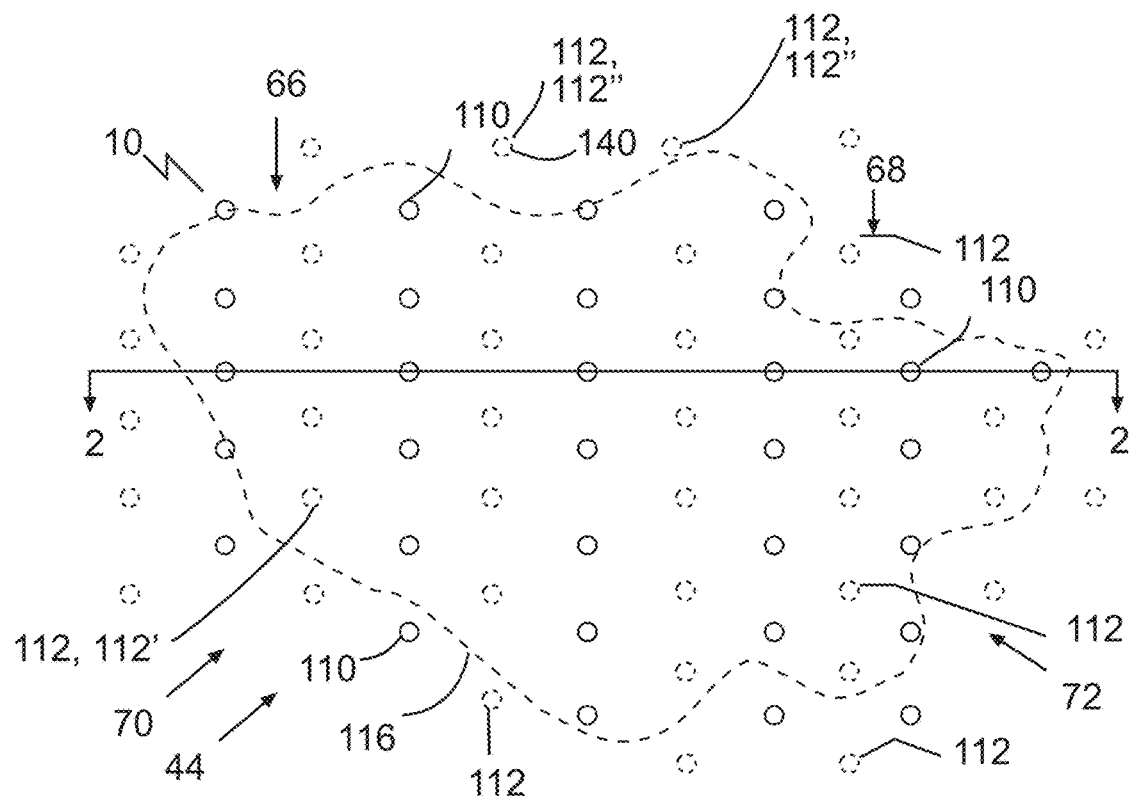
FIG. 1 is a top plan view of an impacted site, with a plurality of injection wells shown in solid lines, and an underground volume of hydrocarbon contaminated soil and a plurality of sensor wells shown in dashed lines.

Immaterial modifications may be made to the embodiments described here without departing from what is covered by the claims.

Hydrocarbon contamination exists in groundwater and soil at thousands of sites around the world. This contamination is often the result of accidental release of fuels (e.g. gasoline or diesel fuel), or fluids and material (crude oil, drill cuttings) from drilling operations storage, transport, or transfer devices including, but not limited to storage terrestrial treatment cells, tanks, pipelines, dispenser pumps, rail cars, and tank trucks. These contaminants may be detrimental to a natural ecosystem that may interact with a contaminated region, or contaminated material, and/or may pose health hazards for humans, animals, wildlife, the environment, and/or ecosystems.

Attempts to remediate contaminated soil and/or groundwater by a variety of means have been made. Two of the existing methods of remediation of contaminated soil and/or groundwater are chemical treatment and biological treatment. Typically, chemical treatment consists of oxidation of the contaminants via application of remedial additives such as hydrogen peroxide, Fenton reagents, ozone, sodium or potassium permanganate or bisulfate. Typically, biological treatment (bioremediation) consists of stimulating (biostimulating) microorganisms that are either naturally occurring at or near the treatment location or introducing cultured microorganisms into the treatment area.

Bioremediation involves the leveraging and stimulation of microorganisms, such as bacteria and fungi, which are able to consume a portion of the hydrocarbon contaminants as part of natural respiratory processes. This consumption may decompose or degrade the contaminants into less harmful and/or benign respiration products, decreasing contaminant concentration within, or cleaning, the contaminated region, and may take place using aerobic and/or anaerobic reaction pathways. For bioremediation to occur, a contaminated region must include a microbial population that is adapted to metabolize a contaminant, as well as an energy source, a carbon source, an electron acceptor (or oxidant), nutrients, and suitable environmental conditions such as temperature, pH, salinity, pressure, contaminant concentration, and/or an inhibitor concentration within the treatment zone.

Bioremediation may be performed both in situ and/or ex situ. In situ bioremediation includes treating the contaminated material without removal from its current, existing, or natural location, while ex situ bioremediation includes removal of the contaminated material from its current, existing, or natural location for treatment on the contaminated site (such as in land farming) or at a different site. One remediation approach for these soils is to stimulate soil organisms to degrade hydrocarbons by adding nitrogen, phosphorus, and electron acceptors (e.g., nitrate, ferric iron, or ferric sulfate). This approach works ex-situ but often fails in situ, perhaps due to limited microorganisms, electron acceptors, or nutrients. Some additional problems encountered with such bioremediation include keeping the bacteria alive until the pollutants reach the bacteria, or until they reach the hydrocarbon pollutant which is the food source, as well as the difficulty of controlling oxygen content, nutrient levels and temperature in dense, packed soil under the ground surface.

Figure 2:
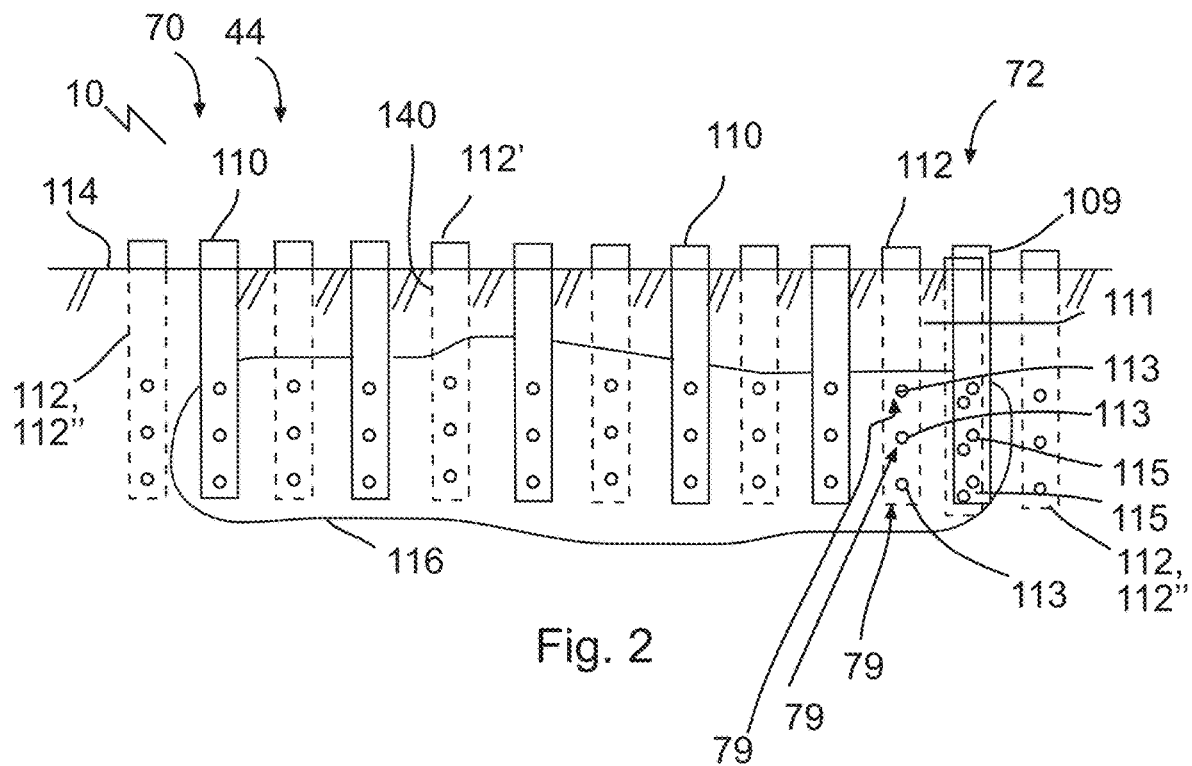
FIG. 2 is a cross section view taken along the 2-2 cross section lines in FIG. 1.
Figure 3:
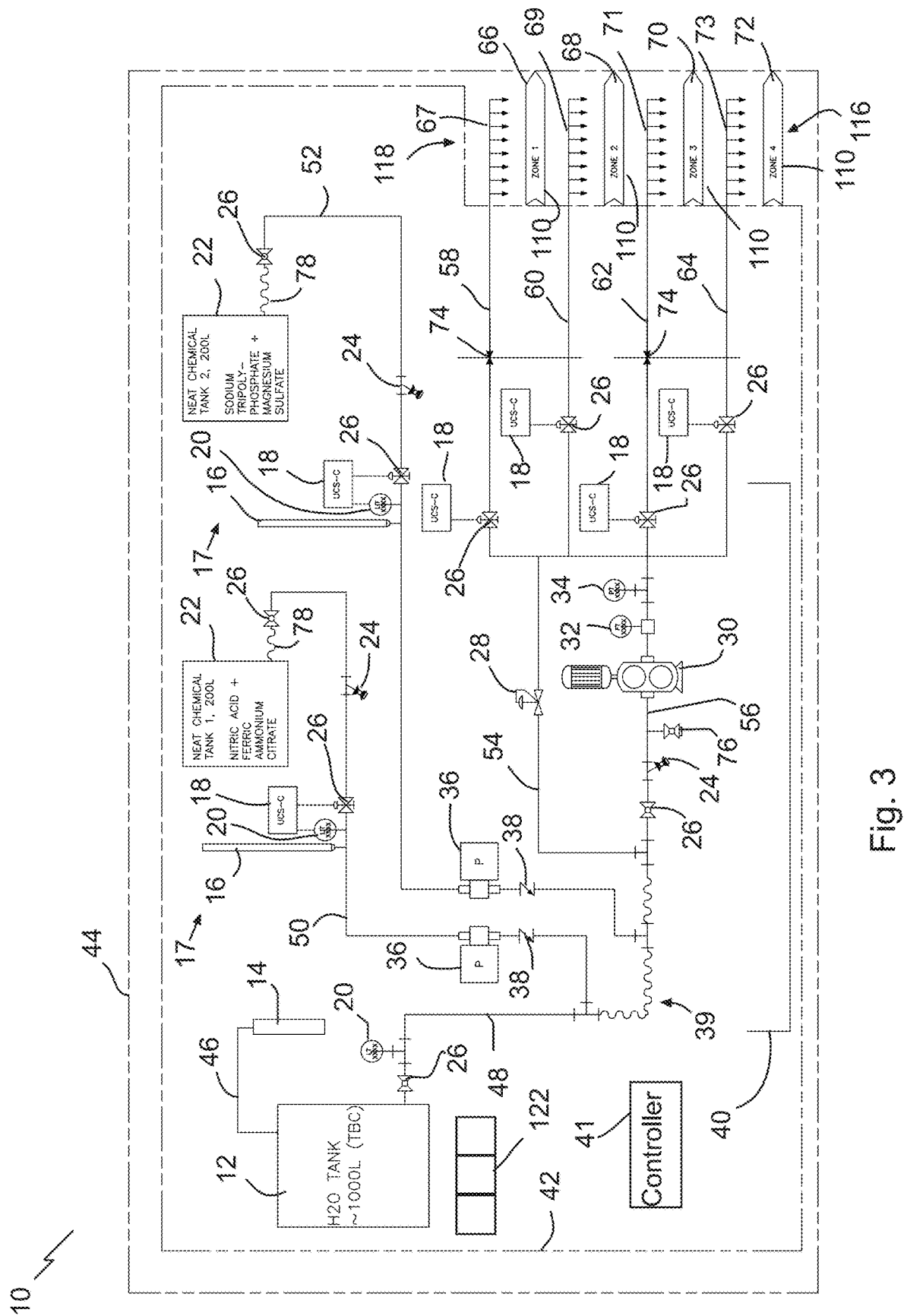
FIG. 3 is a schematic view of a system for bioremediating of hydrocarbon contaminated soils at an impacted site.

Referring to FIGS. 1-3 a system 10 and method are disclosed for in situ treatment of hydrocarbon contaminated soil 116 at an impacted site 44. The system 10 may comprise a plurality, such as a network, of injection wells 110. The plurality of injection wells 110 may penetrate hydrocarbon contaminated soil 116 below a ground surface 114 at the impacted site 44. The wells 110 may also penetrate the ground surface adjacent to hydrocarbon contaminated soil, for example above or laterally to the side of, or below, such soil. The system 10 may comprise a plurality, such as a network, of hydrocarbon depletion sensor wells 112. The sensor wells 112 may be arranged within the network of injection wells 110, for example adjacent to. In some cases the sensor wells 112 and injection wells 110 may be the same wells. The hydrocarbon depletion sensor wells 112 may penetrate the hydrocarbon contaminated soil 116 below the ground surface 114 at the impacted site 44. The wells 112 may also penetrate the ground surface adjacent to hydrocarbon contaminated soil, for example above or laterally to the side of, or below, such soil. A controller 41 may be connected to receive sensor data from the hydrocarbon depletion sensor wells 112. The controller 41 may be connected to control the injection of liquid chemicals into the soil 116 via the injection wells 110. The controller 41 may be connected to control an injector, such as pump 30, to dispense liquid chemicals into the hydrocarbon contaminated soil 116 via the injection wells 110. The system 10 may comprises one or more chemical reservoirs 22, such as liquid chemical reservoirs, for providing chemicals that are injected as liquid chemicals via injection wells 110. The liquid chemicals may be selected to biostimulate a microbial degradation process of hydrocarbons to remediate the impacted site 44. Referring to FIGS. 1-3 in use various steps are carried out. Liquid chemicals may be injected in situ through a plurality of injection wells 110 into the hydrocarbon contaminated soil 116. The injection of liquid chemicals may be controlled by the controller 41. The microbial degradation process may be monitored using a plurality of sensor wells 112, which are located within the hydrocarbon contaminated soil.

The methods and systems 10 of this document may be carried out at suitable locations. For examples, the impacted site 44 may be a former or current fuel dispensing station. In some cases the site 44 may be a former or current oil and gas producing well site. In some cases the site 44 may be a former or current pipeline right of way, a fuel storage facility, such as a bulk storage facility, or any site with current or previous activities that resulted in the release of hydrocarbons onto a ground surface or into a ground subsurface. The site 44 may be any location where hydrocarbon contamination has occurred, for example due to a spill or to migration of contamination onto site 44 from adjacent properties.

Referring to FIGS. 1 and 2, the method and system 10 may include placement of wells 110 and 112 in suitable locations. The method may comprise drilling and installing one or more of wells 110 and 112. The hydrocarbon contaminated soil 116 may be bounded by and defines a volume of soil (delineated by dashed lines) under the ground surface 114 at the impacted site 44. The method may comprise determining boundaries of the volume of soil 116, for example using a geotechnical analysis, which may incorporate core sampling at various depths and locations around site 44 to determine the plume dimensions of the soil 116. Drilling and installing may comprise distributing the plurality of injection wells 110 about the volume of soil 116 to provide adequate coverage of the entire volume, for example to permit the subsequent injection of the liquid chemicals to saturate the volume of soil 116. The sensor wells 112 may be located adjacent the injection wells 110, for example wells 112 may be staggered between adjacent injection wells 110. In some cases, the contamination may be located such that the plume is considered unbounded or unboundable, for example if the soil stretches to a neighboring site that cannot be accessed for the purpose of remediation, or if the contamination extends below a specific depth beyond which remediation is not possible or not required or desired to be remediated.

Referring to FIGS. 1-2, the injection wells 110 may be positioned and installed to suitable specifications. The plurality of injection wells 110 may be arranged at suitable separation distances, such as 3-4.5 m apart from one another, or larger or smaller separation distances depending on the porosity and consistency/structure of the underlying soil 116. The wells 110 may be installed to 2-3 m below the ground surface 114, or deeper or shallower depths depending on the location and dimensions of the volume of contaminated soil 116. In the example shown, the wells 110 are located in a grid or matrix pattern, although other patterns may be used. Sensor wells 112 may be located in gaps between the injection wells 110, for example in the center of each group of four wells 110. Gapping the wells 110 and 112 as shown, and in some cases locating the sensors wells further away from the injection wells than shown, may avoid negative water effects on sensor readings. A water effect refers to the situation where there is a restriction of gas diffusion and advection due to the filling of soil pores with water—in such a case the gas readings would be erroneous. Wells 112 may be located in contact or close proximity with each well 110 in some cases.

Referring to FIGS. 1-3 each injection well 110 may have a suitable structure. Each well 110 may comprise injection tubing 109, with one or more (in the example shown three) injection ports 115. In some cases plural perforations of the tubing 109 may be used as a port 115. Plural ports 115 may be used, for example longitudinally spaced along the injection tubing 109 at different respective depths in the injection well 110. Each port 115 may comprise a filter, for example a fluid permeable pack, to prevent infiltration of solids, which may plug the port 115. In some cases the filter may include a fluid impermeable pack, such as a bentonite pack, separating the axially spaced ports 115. A fluid impermeable screen or other barrier may be used to isolate the different depths of ports 115 along the tubing 109. One or more valves, such as check valves to prevent formation flowback, may be used on the tubing 109.

Referring to FIGS. 1-7 each depletion monitor or sensor 140 may have a suitable structure. Each well 112 may comprise sensor tubing 111 (which may in use be located within the well 112), with one or more (in the example shown three) sensor modules 79. Each sensor module 79 may be on or within, for example may form part of, the sensor tubing 111. Referring to FIGS. 2 and 7, the sensor modules 79 may be longitudinally spaced in series along the sensor tubing 111 at different respective longitudinal positions, which correspond to different respective depths of each sensor module when the depletion sensor 140 is in use inserted within underground soil 116 below a ground surface 114. Referring to FIGS. 4-7, a sensor module 79 may comprise a sensing part, such as one or more sensors 80, 81, 82, 83, 84, 85, 87, and 91. The sensing part may be located within a suitable housing 86, such as a waterproof housing, such as made with polyvinyl chloride ("PVC"). The use of a waterproof housing with a vapor permeable membrane may allow the module 79 to be used as part of a water monitoring solution, to monitor groundwater. The housing 86 may be equipped with a membrane, such as a silicone membrane, that may be permeable to gases but not liquids, which may exclude water from the sensor module housing 86. The sensing part may be located on or within (within is shown) the sensor tubing 111. The housing 86 may be formed by a portion of the tubing 111. The module 79 may have or be associated with a port 113 in the housing, such as a port 113 in the sensor tubing 111, that puts the sensing part in fluid communication with the exterior of the sensor tubing at the respective longitudinal position of the sensor module 79. A fluid permeable filter, such as a sand pack, may be between the sensing part and the port 113. In some cases plural perforations of the tubing 111 may be used as a port 113. Plural ports 113 may be used, for example longitudinally spaced along the tubing 111 at different respective depths in the sensor well 112. In some cases a fluid impermeable barrier or pack, such as a bentonite pack, may separate the longitudinally (also referred to as axially) spaced sensors in the tubing 111. Each sensor pack may be surrounded by a clean sand pack and sealed from other sensor packs (sensor modules 79) in the profile with bentonite to ensure accurate data that is directly related to the installation depth. A fluid impermeable screen may be used in such a case to prevent the different sensing depths from cross talking with each other. More generally, a bore wall sealing part, such as an o-ring 94 (a type of gasket) circumferentially extending around the tubing 111, may be on the exterior of the sensor tubing 111 longitudinally separating adjacent sensor modules 79. Seals, such as O-rings 94, may be used to seal an external surface of the housing 86 to the bore of the tubing 111 or in the example shown well 112. Without some kind of seal or barrier longitudinally isolating the sensors in the tubing 111, the borehole (well 112) may act as a pathway to the surface, and the measured gas concentrations are in equilibrium with the atmosphere, not via the soil, but via the borehole tube—technically, this is referred to as preferential flow paths. One or more valves, such as check valves to prevent formation flowback, along the tubing 111 other than to the sensing part or parts. Where plural sensor modules 79 are used on a tubing 111, the sensor modules 79 may be longitudinally spaced along the sensor tubing 111 at different respective depths in the sensor well 112.

Referring to FIGS. 4-7, suitable depletion sensors 140 may be used. Each of the depletion sensors 140 may comprise one or more of an oxygen sensor 80, a carbon dioxide sensor 82, a methane sensor 85, a hydrocarbon sensor 84, a temperature sensor 83, an electrical conductivity (pH) sensor 81, and a humidity sensor 87. Other sensors 91 may be used (FIG. 6). In the example of FIGS. 4-5, the module 79 has an oxygen sensor 80, a carbon dioxide sensor 82, and a hydrocarbon sensor 84. In the example of FIG. 6, the module 79 has all of the above sensors. In the example shown, the housing 86 is indented or has a cutout to define a receptacle 99, which may one or more of locate the sensors, and may define a volume of space to contain a fluid permeable filter pack (not shown). The sensors may be mounted or otherwise connected to a printed circuit board 92 with electronics for operating the sensors. The cutout may be such that a planar board 92 may be situated, for example nested longitudinally as shown, within the tubing 111. A cover 90 may mount upon and protect the board 92. Electrical contacts 89 may be positioned at one or both ends of the housing 86 to permit transmission of the sensor data uphole. In some cases a wireless transmitter is included to transmit sensor data, for example using a cellular transmission, to a remote controller or other receiver. A controller 41 (FIG. 3) may be connected to one or both store and receive data from, the sensor modules 79. The controller may comprise a transmitter for transmitting data from the sensor modules 79 to a remote location. Each module 79 or depletion sensor 140 may include a controller. An aboveground solar power source, such as solar collector 122 (FIG. 3) may be connected to power the sensor modules. One or more end caps 88 may be used, for example to define a tubing connector 93.

Referring to FIGS. 4-7 a sensor 140 may have suitable characteristics. For example a housing 86 may be used to provide an example of a structural frame to mount the various internal components of the module 79. Each end of the housing may comprise a tubing connector 93, for securing, for example threading, to sensor tubing 111. In other cases the module 79 may fit within for example nest within the tubing 111. Referring to FIG. 7, a sensor 140 may include plural sensor modules 79 arrayed at different longitudinal positions along the length of the sensor tubing 111, for example between a top and base end 140A and 140B, respectively.

Referring to FIGS. 9-10, another example of a sensor module 79 is illustrated with different sensors that may be assembled together. A multichannel infrared sensor 188 may be used to measure one or more of methane, carbon dioxide, and volatile hydrocarbons. The infrared sensor 188 may have a sample chamber 174 to collect a sample, a detector 176, an amplifier 178, a multiplexor 180, and pin headers 182 (on a printed circuit board as shown) that work together to measure different compounds such as methane, carbon dioxide, and volatile hydrocarbons. The infrared sensor 188 may have one or more mounting nuts 184 to attach the sample chamber 174 with the detector 176 and other parts of the sensor 188. Referring to FIG. 9, an oxygen sensor 80 and a photoionization detector 194 are also shown in the example. The photoionization detector 194 may estimate aromatic hydrocarbon vapors with relatively low detection limits. A microcontroller 172 may also be included in the module 79 to control the various parts and receive and process data therefrom. A suitable connector, such as a cat5e (category 5 cable) connector 156 may also be present on the ends of the sensor module 79 to transmit collected data the sensors to a communication module 146 for further data transmission. Category 5 cable (Cat 5) is a twisted pair cable for computer networks. Since 2001, the variant commonly in use is the Category 5e specification (Cat 5e). The cable standard provides performance of up to 100 MHz and is suitable for most varieties of Ethernet over twisted pair up to 2.5GBASE-T but more commonly runs at 1000BASE-T (Gigabit Ethernet) speeds. Cat 5 is also used to carry other signals such as telephone and video. Other communication cables and related connectors may be used. Each sensor module 79 may be equipped with a lead-free oxygen sensor 80, temperature and pressure tytsensor 83, humidity sensor 87, and other sensors 91 (such as a pressure sensor), providing a complete picture of the below-ground environment.

Referring to FIG. 13, the depletion sensor 140 (also known as a quantifier) may have a suitable structure. The depletion sensor 140 may be installed into a borehole (an example of well 112) of suitable construction, such as a 4-6 inch diameter. Into the well 112 may be installed the sensor tubing 111 of suitable construction, such as 2 inch diameter PVC pipe, that has been lined with one or more depletion sensor well screens 192 of suitable size, such as 2-inch diameter length PVC screen that extends 14 inches. The well screen 192 may be slotted at the respective depths where the sensor modules 79 are located. Each sensor housing 86/module 79 may be connected axially along a connector tubing 111 of suitable construction, such as 1 inch diameter PVC pipe, to form a suitable data transfer pipeline. This may allow gases to enter from the soil, into the well screen 192, and eventually into sensor module housing 86, where they can be measured. Each sensor module 79 may be surrounded by a clean sand pack 144 and sealed from other sensor modules 79 in the profile with a bentonite layer 142 of suitable construction to ensure accurate data that is directly related to the installation depth. Each module 79 may have an airlock at each axial end to prevent gas and liquid communication axially.

Referring to FIG. 13, a gas delivery tube 186 may be included in the sensor well 112 and may allow direct estimates of soil permeability, for example to occur on a periodic basis such as an annual basis. The tube 186 may be of suitable construction, such as a ¼ inch stainless steel soil, and may act as a soil vapor probe for permeability estimates. The gas tube 186 may be used to assess site specific permeability for each sensor pack/module 79. Permeability is a measure of readily gas can diffuse through a medium. One or more additional tubes, such as a second tube 187, may be installed inside the well 112 to sample other characteristics/parameters, such as groundwater. In the example shown in FIG. 13, the well 112 may have a gas tube 186 as well as a water sampling tube 187 that may be used to sample groundwater present in the installation well 112.

Referring to FIGS. 4-6 the various sensors may detect various properties of the soil, either in a general monitoring process, or as part of a remediation process. An oxygen sensor 80 may detect levels of oxygen in the soil, denoting whether the remediation process is proceeding aerobically or anaerobically. The carbon dioxide and methane sensors 82 and 85, respectively, may detect levels of carbon dioxide and methane, which are expected to rise as the bioremediation process initiates, as waste products of the metabolic pathway of the microbes. A hydrocarbon sensor 84 may detect levels of hydrocarbons, for example aliphatic, aromatic, or other types of hydrocarbon molecules or groups of types of molecules. The temperature sensor 83 may measure temperature in the soil, which is expected to rise as the bioremediation process initiates and the microbes increase activity and metabolism of hydrocarbons, releasing energy in the form of heat. A typical rise from initiation of such a process is 3-4 degrees Celsius. A pH sensor 81 may detect pH levels in the soil, expected to drop slightly as the bioremediation process initiates and the metabolism of the microbes releases acidic byproducts. A humidity sensor 87 may detect water levels in the soil. In order to ensure that the bioremediation process proceeds smoothly, water is required to allow permeation of liquid chemicals to and byproducts from the microbes, so soil moisture is needed.

Referring to FIGS. 1-7, in some cases depletion sensors 140 may be used independent of an remediation liquid injection process. In such a case, injection wells 110 may or may not be present, at the site, or may be present but not used. A network of depletion sensor wells 112 may penetrate the ground surface, with each of the depletion sensor wells 112 containing a depletion sensor 140. In such a use, the sensors 140 may monitor, over an extended period such as days, weeks, months, or years, levels of carbon-containing compounds in the underground soil 116. During such monitoring, over the extended period of time, the sensors 140 may remain at different locations within the underground soil 116 at the site, with a plurality of sensors (sensor modules 79) located at one or more isolated depth zones along the respective depletion sensor well 112. The plurality of sensor modules 79 may take continuous or periodic readings over the extended period. The controller or controllers 41 may be connected and configured to one or more of: collect the data continuously or at intervals; store the data locally; and transmit the data. Where injection wells 110 are also present, though not required, such may be used continuously or intermittently as needed in tandem with the data from the sensor wells 140. A depletion sensor 140 may measure one or more of soil gas, $CO_2$, $CH_4$, $O_2$, and Volatile Organic Compounds concentrations as well as temperature and moisture, at, a least, two, three or more discrete depths in the soil. This information may be collected at suitable intervals, such as high frequency intervals, such as once per minute, and then stored locally or transmitted back to a data storage facility. The depletion monitors (sensor 140) may be designed to be inserted directly into an existing soil borehole that may have been drilled for assessment. The depletion sensor may use a mechanical means to separate out the depths of measurement, such as a circumferential seal 46. The depletion sensor data may be used to estimate the biogeochemical cycling of carbon in the subsurface environment. This carbon may be hydrocarbons but may also be sequestered carbon, such as in the form of absorbed $CO_2$. The data from depletion sensors may be used to estimate hydrocarbon depletion and/or carbon cycling in the subsurface. The estimates of hydrocarbon depletion do not require a site to be undergoing active remediation but may be used as a means of monitoring a sites activity. In some cases, at least two depletion sensors are used at a site. One may be in a reference location, typically not contaminated with hydrocarbons, and one in the center of pollutant mass, see FIGS. 1 and 2 as examples of such sensor wells 112" and 112', respectively. In the examples of FIGS. 1 and 2, the depletion sensor wells 112 include wells 112' that are inserted into the hydrocarbon contaminated soil 116. The depletion sensor wells 112 may include wells 112" that are inserted into underground soil adjacent to the hydrocarbon contaminated soil 116. The injection wells 110 may be positioned inside and outside the contaminated soil 116 in some cases, in a fashion similar to that shown for the sensor wells 112. Additional depletion sensors may be deployed if desired, such as in a network as shown.

Referring to FIGS. 1-3, the sensor data from the sensors may be received and used in a suitable fashion. The sensor wells 112 may be connected to send sensor data to the controller 41. The controller 41, which may be one or more controllers 41, may receive the data. The controller 41 may perform various operations on the data, such as storing the data on a computer readable medium, or transmitting the data off-site to a remote computer. In other cases the method comprises adjusting a flux of liquid chemicals in response to the sensor data from the plurality of sensor wells 112.

Figure 12:
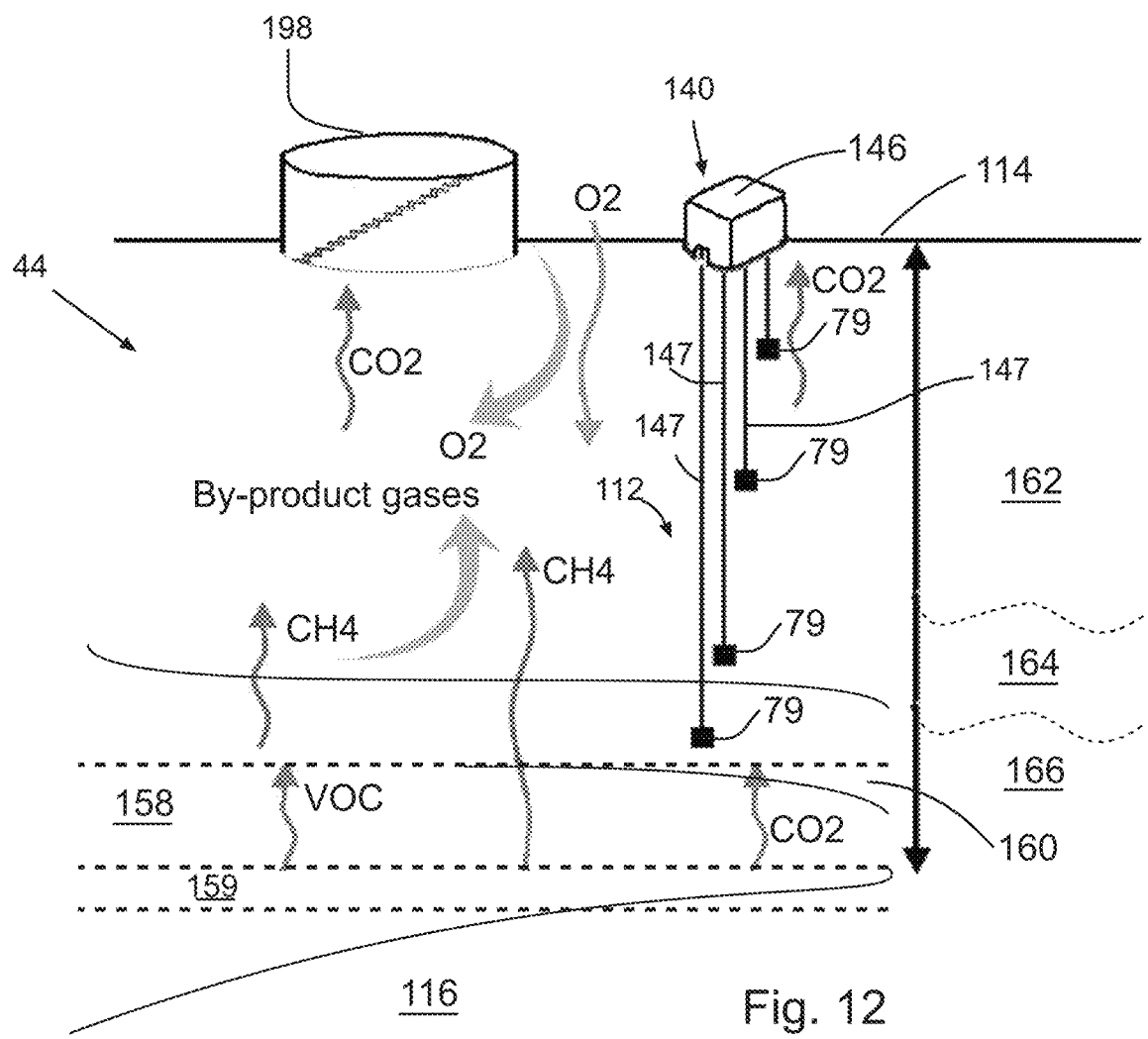
FIG. 12 is a side view illustrating a Natural Source Zone Depletion (NSZD) process that uses a depletion sensor, with sensor modules at different soil depths.

Referring to FIG. 13, a depletion sensor 140 may compile data, which may be transmitted from a data collection site to a data processor 154. As above, depletion sensor 140 may measure one or more of soil gas, moisture, barometric pressure, temperature, and hydrocarbons. From such parameters, the depletion sensor 140 data may be used to estimate biological activity, hydrocarbon depletion and hydrocarbon concentrations at suitable intervals, such as every 30 minutes throughout the year. Depletion sensor 140 may contain several sensor modules 79 that are placed down the soil profile, providing an estimate of gas flux to the atmosphere. Referring to FIGS. 12-13, sensor modules 79 may be connected to each other with suitable connector cable 147 running inside. The cable 147 may be terminated above ground where it may connect to a top communication module 146. Sensor modules 79 communicate with each other and with the communication module 146 by a suitable method, such as serial communication protocol, allowing any number of sensor packs to be chained together. The sensor modules 79 may communicate with the top communication module 146, which may contain suitable parts for data transmission such as a GPS (Global Positioning Satellite) module, a temperature sensor, a battery voltage sensor and a Long Range ("LoRa") chirp spread spectrum communicator. The communication module 146 may compile the results from the various sensors 79, then transmit the collected data by a suitable method, such as LoRa communication protocol. By using LoRa communication or similar methods for data transmission, the depletion sensor 140 may be used in remote areas, away from permanent infrastructure, relying on solar power and/or batteries. For developed areas, the depletion sensor 140 may be powered by long-life batteries alone, minimizing above-ground infrastructure and only requiring yearly service to change the batteries.

Referring to FIG. 12, the exchange of gases in an impacted site 44 may be studied to characterize natural source depletion zone (NSZD). An impacted site 44 may comprise of different soil layers, such as a dissolved plume 116, capillary zones 158 and 159, anoxic zones 166, aerobic zones 168, and other zones such as an oxic zone 162, distinguished by distinct biodegrading processes. Different gases may be present in each layer, depending on the biodegrading process occurring in each layer. An oxic zone 162 may be rich in oxygen coming from the ground surface 114, and where aerobic respiration may be occurring. An aerobic biodegradation front 164 may be beneath the oxic zone 162 and may be the deepest layer where aerobic degradation may occur and may transition towards the anoxic zone 166 where anaerobic degradation may occur. A hydrocarbon impact zone 160 may be collected on top of the capillary zone 158. Released gases from the soil may be collected at surface via a suitable collector 198.

Referring to FIGS. 12-14, the data from the sensor 140 may be analyzed (quantified) off-site by suitable methods. Referring to FIG. 13, the data may be transmitted to one or more network servers 150 and may be analyzed using various programs (code modules run on one or more processors 154). The depletion sensor 140 data may be used to estimate NSZD rates at each location using a suitable method, such as the concentration gradient method. Understanding the change in NSZD rates over time may help provide a more accurate site-specific rate than traditional NSZD measurement techniques. Further, depletion sensors 140 placed on the plume 116 fringe may not only provide information on NSZD rates but may also be used to monitor mass reductions on the plume fringe. This information may be used for suitable purposes, such as to provide Nichols and Plains-Midstream, with real-time information on environmental and financial liabilities presented by the LNAPL (light non-aqueous phase liquid) and petroleum hydrocarbon plume. Referring to FIG. 13, the data from the communication module 146 of the depletion sensor 140 may be received by a concentrator 148 to prepare for data transmission to a network server 150. Referring to FIGS. 13-14, the network server 150 may send the data to an application server 152 where it may be processed and analyzed. Referring to FIG. 14, a processor 154 such as on a notebook, running a data downloader program module(s) 168, such as Jupyter™ and Python3™, may compile and send the data to an NSZD calculator program module 170, where the data may be analyzed and calculated to obtain suitable measurements, such as steady-state diffusive flux, impacted-background information, corrected diffusive flux, stoichiometric conversions, and NSZD calculations. Various NSZD formulae and an example dataset may be found on the example below:

1.

$$J = D_v^{eff}\left(\frac{dC}{dZ}\right)$$

J=steady state diffusive flux (g/m²-soil/s)
$D_v^{eff}$=effective vapour diffusion coefficient (m²/s)
dC/dZ soil gas concentration gradient (g/m³-m)

2. $J_{impacted} - J_{background} = J_{corrected}$

3. Stoichiometric conversion: benzene-$CO_2$
$2C_6H_6 + 15O_2 \rightarrow 12CO_2 + 6H_2O$
$2C_6H_6$: 2*(12,011 g/mol*6+1.008 g/mol*6)=156.223 g/mol
$12CO_2$: 12*(12.011 g/mol+15.999 g/mol*2)=528.096 g/mol
When 156 g of $C_6H_6$ are consumed, 528 g $CO_2$ are produced
$Stoich_{CO_2}$=156/528

4. Natural Source Zone Depletion
$NSZD = J_{corrected} * Stoich_{CO_2}$

Figure 15:
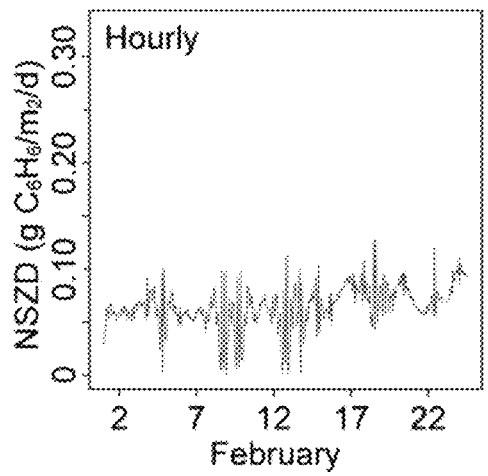
FIGS. 15-18 are graphs illustrating different ways of presenting a dataset collected by a depletion sensor.
Figure 16:
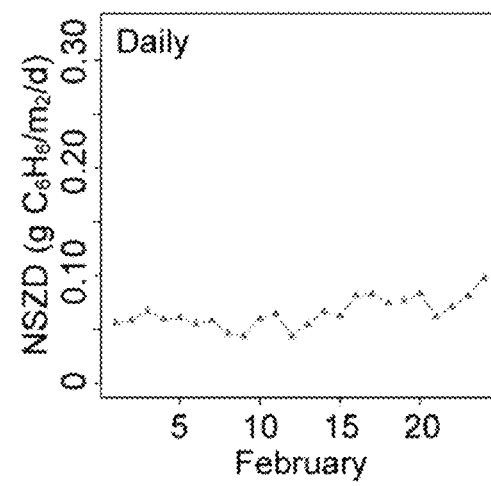
Figure 17:
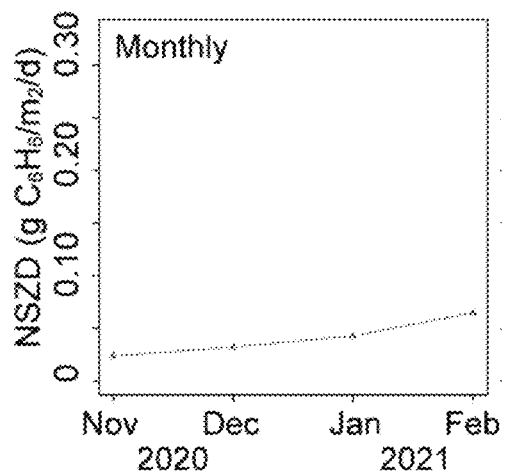
Figure 18:
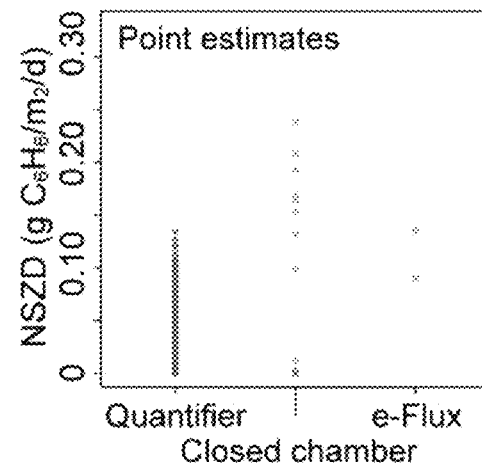

Referring to FIGS. 15-18, the NSZD rates calculated from data collected from a depletion sensor 140 may be plotted and analyzed in several ways. Referring to FIG. 15, hourly data of NZSD rates is shown. Referring to FIG. 16, daily data of NZSD rates is shown. Referring to FIG. 17, monthly data of NZSD rates is shown. Referring to FIG. 18, point estimates of NSZD rates is shown in different contexts such as a quantifier, a closed chamber, and an e-Flux.

The data measured and analyzed may be used to determine site permeability estimates. Soils are permeable materials because of the existence of interconnected voids that allow the flow of fluids when a difference in energy head exists. A good knowledge of soil permeability is needed for estimating the progress of a natural or enhanced soil remediation process. Soil permeability is also termed hydraulic conductivity. The measurements herein may be used for other purposes such as to assess soil quality to optimize agriculture productivity.

Referring to FIGS. 1-3, the controller may adjust the injection of the liquid chemicals in response to the sensor data from the plurality of sensor wells 112, for example to maintain a rate of the microbial degradation process within a predetermined range. The system 10 may have associated with it an optimal range of progression for the remediation, as reflected in the various sensory properties that can be observed by each module 79. If the system 10 is underachieving (below the range), then various steps may be taken to attempt to increase the performance. If the system 10 is overachieving (above the range), then various steps may be taken to decrease performance, for example to prevent various negative outcomes associated with over performance, such as a nitrogen bloom or over saturation/eutrophication of the soils 116.

Referring to FIGS. 1-3 in some cases adjusting the flux may further comprise increasing one or more of a concentration of liquid chemicals and a flow rate of the liquid chemicals through the wells 110. Such a result may be desired if one or more of oxygen levels or a rate of change of same are outside of, for example above, a predetermined range (highly aerobic formation environment); carbon dioxide levels or a rate of change of same are outside of, for example below, a predetermined range (potential underperformance of the remediation process); methane levels or a rate of change of same are outside of, for example below, a predetermined range (potential underperformance of the remediation process); hydrocarbon levels or a rate of change of same are outside of, for example above, a predetermined range (potential underperformance of the remediation process); temperature levels or a rate of change of same are outside of, for example below, a predetermined range (potential underperformance of the remediation process); pH levels or a rate of change of same are outside of, for example above, a predetermined range (potential underperformance of the remediation process); or humidity levels or a rate of change of same are outside of, for example below, a predetermined range (insufficient water in the formation for the process to operate at optimum or sufficient capacity).

Referring to FIGS. 1-3, in some cases adjusting the flux may further comprise decreasing one or more of a concentration of liquid chemicals and a flow rate of the liquid chemicals through the wells 110. Such a result may be desired if one or more of oxygen levels or a rate of change of same are outside of, for example above, a predetermined range (anaerobic formation environment, which in some but not all cases is not desired); carbon dioxide levels or a rate of change of same are outside of, for example above, a predetermined range (potential overperformance of the remediation process); methane levels or a rate of change of same are outside of, for example above, a predetermined range (potential overperformance of the remediation process); hydrocarbon levels or a rate of change of same are outside of, for example below, a predetermined range (potential overperformance or almost completion of the remediation process); temperature levels or a rate of change of same are outside of, for example above, a predetermined range (potential overperformance of the remediation process); pH levels or a rate of change of same are outside of, for example below, a predetermined range (potential overperformance of the remediation process, or potential indicator that the composition of the liquid chemicals requires adjusting); or humidity levels or a rate of change of same are outside of, for example above, a predetermined range (too much water in the formation for the process to operate at optimum or sufficient capacity).

Referring to FIGS. 1-3, adjusting or setting the flux may be based off of suitable predetermined ranges of variables. The predetermined ranges may be site-specific and may be adjusted as remediation process proceeds. In some cases a rate of change of variables is measured. The change in concentrations may be monitored throughout the injection and over time. When there is little to no change, system parameters may be changed, for example injection rate or concentration may be increased to attempt to stimulate the process. The flux of gas may be measured, for example in g of gas/m$^2$ of soil per second. When a rate of change is large, the injection and concentration parameters may level off or decrease to avoid saturating or overloading the system. In one case the predetermined range of temperature is 3-4 degrees above an initial ambient soil temperature at or adjacent the impacted site 44. Ambient temperature may change depending on season so a calibration step may need to be carried out periodically to adjust the temperature range. The predetermined range of pH may be between 4 and 9, for example being between 6 and 9. In some cases the predetermined range of pH may be below initial ambient soil pH at or adjacent the impacted site, as an increase in pH may indicate $CO_2$ being produced, reflecting a remediation process occurring. The predetermined range of humidity may be between 0% and 40%. Humidity levels may affect the accuracy of the sensors. In some cases the sensors work best at low humidity levels (for example between 0%-10%). Some sensors may have a built-in algorithm to compensate for effects of humidity. In some cases membranes on the sensor housings may have a lower permeability to water vapor than to other gases, and such might keep the sensors in relatively low humidity—however, in some such cases an equilibrium will still be reached with humidity under stable conditions. The predetermined range of methane may be between 0% and 20% for example between 0% and 9.3%. The predetermined range of oxygen may be between 0% and 21%, for example between 0.4% and 20.9%. In many cases oxygen will decrease with depth and never exceed ambient conditions. The predetermined range of $CO_2$ may be between 0.03% and 520%, for example between 0.3% to 18.4%. $CO_2$ may be near ambient concentrations near the surface (for example 400 ppmv) and may increase with depth. The sensors may come with plural, for example 3, adjustable ranges, and one useful range may be between 0%-1%. In some cases 400 to 500 ppm $CO_2$ may be measured. The predetermined range of volatile organic compounds (VOC)s may be between 0% and 5%, for example between 0% and 0.15%. VOCs may have highest concentration just above the hydrocarbon impact zone and decrease as the depth decreases. VOCs may have the same ranges as $CO_2$. The predetermined range of temperature may be between 20 and 40 degrees Celsius. Adjusting may further comprise one or more of: increasing one or more of a relative proportion and injection rate of water in the liquid chemicals if humidity levels are below the predetermined range; and decreasing one or more of a relative proportion and injection rate of water in the liquid chemicals if humidity levels are above the predetermined range. Non-zero extreme upper or lower values of ranges of values in this document include the non-zero extreme upper or lower value. The values given in ranges in this document are exemplary and do not exclude other values outside (above or below) the range being excluded.

Referring to FIGS. 1-3, the controller 41 may operate the method and system 10 based on or more of prior programming, feedback from sensor data, and remote influence by a user. The controller 41 may comprise a transmitter that wirelessly transmits, for example using a cellular or WiFi service, and receives control signals to and from an off-site central computer. The off-site central computer may perform calculations, such as using regression analysis or machine learning, to determine what the optimal flux characteristics should be to efficiently operate the bioremediation process. The computer may then transmit such information to the remote controller 41. In other cases, the controller 41 responds directly to the sensor data, for example based on an operation model programmed into the controller 41, which may be a suitable controller such as a programmable logic controller (PLC) or other type of computer.

The controller 41 may be structured to address certain conditions by adjusting (for example cease) operations of any component in the system or sending a warning signal to a user. For example, if low chemical levels are detected in one of the liquid chemical reservoirs, a warning may be transmitted, for example texted, to a user or to the central computer database where such would be brought to the attention of an appropriate user. Other cases where a warning may be issued include, high back pressure in a well 110 indicating a block, low oxygen or low humidity readings, low water level readings in reservoir 12, zero or reduced flow rates in flow meters, loss of line pressure evidencing a leak in the system, a predetermined fill level being reached in a drip pan 40 underlying all or part of the system 10.

Referring to FIGS. 1-3, wells 110 may be segregated into groups. Each group may be treated independent from the treatment of other groups, based on the sensor data received from the sensors of the respective group. Thus, a plurality of injection wells 110 may comprise a plurality of groups, such as groups 66, 68, 70, and 72, of one or more injection wells 110 each associated with one or more respective adjacent sensor wells. The controller 41 may adjust the injection of the liquid chemicals based on the sensor data of the one or more respective adjacent sensor wells independent of the injection to the other groups. Thus, for example, the sensor data from respective sensor wells 112 of group 68 of wells 110 may show an underperformance of the remediation process, whereas data from group 70 shows an overperformance. In such case, injection may be throttled (for example concentration of liquid chemicals increased, flux increased) to group 68, and decreased (for example concentration of liquid chemicals decreased, flux decreased) to group 70, to maintain the process at optimum operation efficiency.

Referring to FIGS. 3 and 7, the injector may be structured to deliver and maintain predetermined flow rates of liquid chemicals into the plurality of injection wells 110. The injector may be structured to maintain such rates for months, for example years, without stopping or interruption. A reliable, long term system 10 may permit the site 44 to be left in operation without a user on site.

Referring to FIGS. 3 and 7, the injector may comprise one or more dosing stations 17. Each station 17 may have one or more liquid chemical reservoirs 22. A suitable dispensing system may be incorporated and operated by each station 17. Each dosing station may comprise, downstream of the respective liquid chemical reservoir 22, a control valve 26, a columnar or other reservoir 16, a pump 36, a sensor 20, and a controller 18. The control valve 26 may be connected to the liquid chemical reservoir 22. The columnar reservoir 16 may be connected to the control valve 26. The pump 36 may be connected to the columnar reservoir 16. The dosing station sensor 20, such as a level transducer or pressure transducer, may be connected to sense level or pressure in the columnar reservoir 16. The injection controller 18 (for example controller 41 in one case) may be connected to the dosing station sensor 20 and connected to operate the pump 36 and control valve 26 to provide a predetermined flow rate of liquid chemical downstream. The example shown forms an uninterruptible chemical supply (UCS) system.

An Uninterruptible Chemical Supply (UCS) system may be a flow and level transmitter that can provide relatively accurate flow rates. The system may work by having the acceptable rates programmed into the control unit (controller 18). The pump 36 flow rate may be verified by continuously analyzing and interpreting discharge pressure patterns surrounding pressure spikes downstream the pump 36. The controller 18 may send a signal to open the chemical supply valve 26 allowing the columnar reservoir 16 to fill. The valve 26 may close when the columnar reservoir 16 is full (for example after a pre-set fill time). The pump 36 may draw chemical from this columnar reservoir 16. When the columnar reservoir 16 reaches a pre-determined "fill" level, the valve 26 may open to refill the columnar reservoir 16. The pump 36 may continue to operate normally while the columnar reservoir 16 is being filled. This cycle may continuously repeat. The change in fluid level in the columnar reservoir 16 over time may be monitored by a very sensitive pressure sensor 20, along with filtering algorithms, to be able to output a very accurate and stable flow rate that is responsive enough to enable closed loop control to a set point (Flow rate or PPM).

Figure 8:
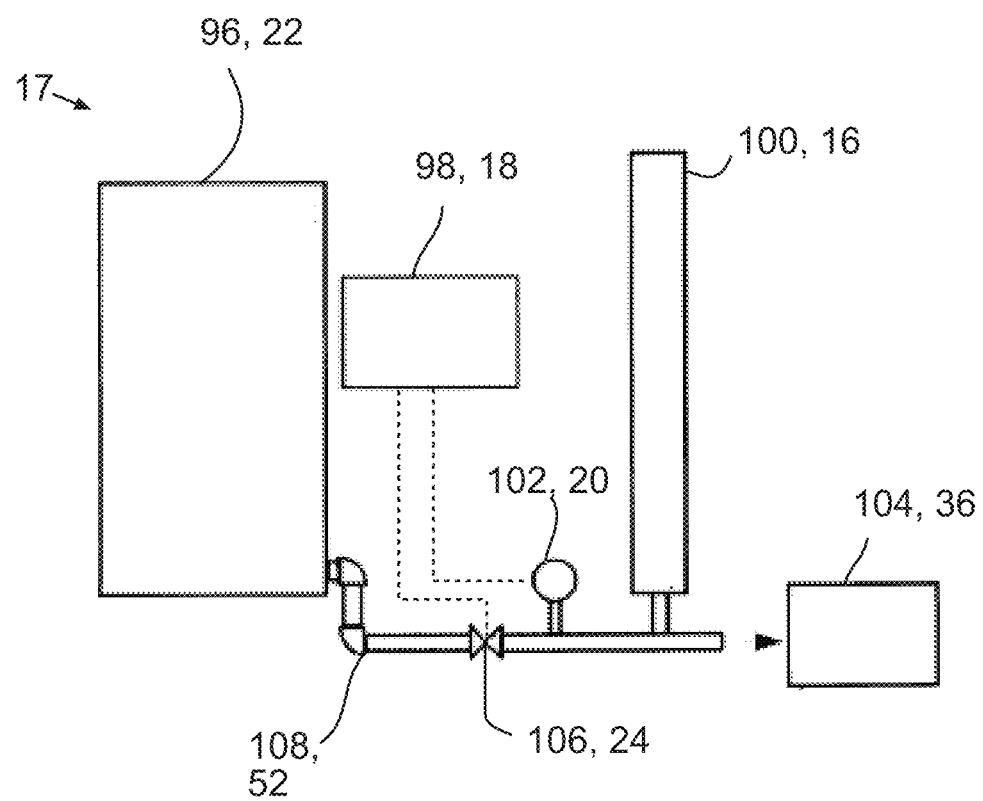
FIG. 8 is a side elevation schematic view of a dosing station of a liquid chemical for use in the system of FIG. 3.

Referring to FIG. 8, there is illustrated another example of a continuous flow chemical metering apparatus (dosing station 17). Station 17 may have a conduit 108 adapted to be connected as part of a chemical injection line down-stream of a chemical storage tank 96 and upstream of a chemical injection device 104 for controlling injection of chemical drawn from the chemical storage tank 96 through the chemical injection line. The chemical injection device 104 may be a valve, pump or another device operated continuously or intermittently. A measuring vessel 100 adapted to hold a column of fluid may be connected to the conduit 108, the measuring vessel 100 being in fluid communication with the conduit 108. An automated valve 106 may be provided for controlling flow through the conduit 108. An automated valve 106 for controlling flow through the conduit 108 may be located upstream of the measuring vessel 100. A means for determining head pressure of the measuring vessel 100, including at least one sensor 102 may be provided. A processor 98 may be provided which is capable of being calibrated to establish calibration data regarding the relationship between head pressure and a height of the column of fluid in the measuring vessel 100. The processor may be adapted to control the automated valve 106 and to receive data from the at least one sensor 102.

Referring to FIG. 8, the processor 98 may control a continuous testing cycle in which the automated valve 106 is closed when the height of the column of fluid in the measuring vessel 100 has stabilized so that chemical drawn by the chemical injection device 104 partially empties the measuring vessel 100. It must be noted, that if the instrument is not intended to determine the fluid level in the chemical storage tank, that an arbitrary predetermined level may be selected, instead of a stabilized level. The stabilization of the height of the column of fluid may be necessary however, in order to establish a relationship between the height of the column of fluid in the measuring vessel 100 and the fluid level in the chemical storage tank 96. After the measuring vessel 100 has been partially emptied, the automated valve 106 may be reopened so that chemical drawn by the chemical injection device 104 device is drawn from the chemical storage tank 96 while the height of the column of fluid in the measuring vessel 100 again has an opportunity to rise. The processor 98 may determine the flow rate by monitoring signals from at least one sensor 102, which may be continuously recorded to memory, and performing calculations using the calibration data and current data regarding dynamic changes to head pressure.

Referring to FIG. 8, in addition to flow rate, the following information, but not limited to, may also be determined and displayed digitally or output via analog or digital signal: storage tank 96 level, loss of fluid, other than fluid passing through the chemical injection device 104 such as leaks between storage tank 96 and automated valve 106. Also, by using measuring vessels 100 with various volumes, heights, sizes, or shapes such as staged and tapered etc., or by using combinations of measuring vessels 100, flow rates from a drip per minute to hundreds of liters per minute may be accurately and very quickly calculated and a change in flow indicated immediately.

Referring to FIG. 3, a mixing station 39 may be provided to dilute chemicals used in the injection process. For example, the injector may comprise the mixing station 39 where the liquid chemical concentrates are diluted with dilution water. Dilution water may be provided from a reservoir 12. Liquid chemicals, such as concentrates, may be dispensed by one or more dosing stations 17 as shown. At the mixing station 39, one or more of the liquid chemicals may be combined with dilution water from line 48. The process of mixing may be similar to that of a fountain pop machine, where final composition (i.e. mixing of components) is achieved immediately prior to injection. Mixing in such a fashion may operate more effectively than pre-mixing. Pre-mixed liquid chemicals may drop out of solution if precipitates are formed due to modified solubility or chemical reaction in the presence of other of the chemicals. Mixing on the fly prior to injection may also be more efficient than providing pre-mixed solution, as concentrates or solid chemicals may be easier to store, dispense, and transport in an unmixed state rather than a mixed state.

Referring to FIG. 3, the dilution water may come from a suitable source. In one case, the reservoir 12 may receive water from an external supply such as a supply truck or municipal supply system if available. In another case, the reservoir 12 may receive supply from a local groundwater source. Thus, the method may include supplying the dilution water to the mixing station from a groundwater supply at the impacted site. For example the dilution water may be pumped to surface using a submersible pump 14.

Referring to FIG. 3, suitable chemicals may be used to biostimulate the hydrocarbon degradation process. The liquid chemicals may comprise one or more of nitric acid, ferric ammonium citrate, sodium tripolyphosphate, and magnesium sulfate. Nitric acid or its salt may be used. Ferric ammonium citrate is a source of citrate, and other sources of citrate may be used. Sodium tripolyphosphate is a phosphate source, and may be substituted or supplemented with another phosphate source. Magnesium sulfate is a salt and sulfate provider and may be substituted with other salts and sulfate providers. Magnesium sulphate is an epsom salt, and may partly neutralize the acidity that is caused when nitric acid is added.

Referring to FIG. 3, the chemicals may be stored in various combinations. In the example shown, a first dosing station 17 (on the left in the figure) may have a liquid chemical reservoir 22 comprising nitric acid and ferric ammonium citrate. A second dosing station 17 (on the right in the figure) may have a liquid chemical reservoir 22 comprising sodium tripolyphosphate and magnesium sulfate. Selectively pre-combining ingredients/chemicals to pre-combine may be based on solubilities and reactivities of the chemicals to be combined. For example, nitric acid and ferric ammonium citrate will not drop out of solution once mixed, and thus are good candidates for pre-mixing. Similarly, sodium tripolyphosphate and magnesium sulfate do not drop out of solution once mixed, and thus are good candidates for pre-mixing. However, if all four ingredients were pre-combined, some precipitation may occur, thus changing flux rates and concentrations. The use of concentrates or solid chemical dispensers (dosing stations 17) also permit larger stocks of liquid chemicals to be stored at site than if fully pre-mixed and diluted liquid chemical compositions were stored and used in the method.

Referring to FIG. 3, relatively low concentrations, flow rates, and pressures may be used in the system 10 and method. Injecting may comprise injecting the liquid chemicals at 1-5 liters per minute. Injecting may comprise injecting the liquid chemicals at between 0 and 10 pounds per square inch (psi). Injecting may comprise injecting at below fracturing pressures, to avoid forming liquid short circuits in the soil 116 for maximum penetration throughout the volume of soil 116. Injecting may comprise injecting the liquid chemicals at 0.1-1 mmol/L. Other suitable concentration, flow, and pressure ranges greater or lower than such ranges mentioned may be used.

Referring to FIG. 3, a suitable power source may be used for the system 10. Where possible, municipal power may be used, for example by connecting the components to a wall plug outlet or other corded source of power. In other cases, solar power may be used. In the example given various parts or all of the method may be carried out using a solar power source. The injecting and monitoring steps may be carried out one or more solar power collectors 122. The use of relatively low pressures and low flow dosing stations 17 make it possible to run the entire system 10 on solar power alone. Solar power may be advantageous as such may enable the system 10 to be run unmanned in a remote location. The use of low delivery pressures with UCS systems may allow AC-Medusa to utilize solar power.

Referring to FIG. 3, a suitable mechanism may be provided to house or otherwise support the various control components. For example, the controller 41 and one or more liquid chemical reservoirs 22 may be located in a transport container 42 that is mounted on or forms part of a wheeled trailer or skid. An intermodal transport container is a large standardized shipping container, designed and built for intermodal freight transport, meaning these containers can be used across different modes of transport—from ship to rail to truck—without unloading and reloading their cargo. Intermodal containers are primarily used to store and transport materials and products efficiently and securely in the global containerized intermodal freight transport system, but smaller numbers are in regional use as well. These containers are known under a number of names, such as simply container, cargo or freight container, ISO container, shipping, sea or ocean container, sea van or (Conex) box, sea can or C can.

Intermodal transport containers exist in many types and a number of standardized sizes, but ninety percent of the global container fleet are so-called "dry freight" or "general purpose" containers, durable closed steel boxes, mostly of either twenty or forty feet standard length, although other lengths may be used. In some cases, transport containers have a range of lengths from eight to sixty feet. Common heights are eight feet six inches and nine feet six inches, with the latter often referred to as High Cube or Hi-Cube containers, although other heights may be used. Common widths are eight feet, although other widths may be used such as six foot three inches, eight foot six inches, or larger or smaller. Transport containers are a means to bundle cargo and goods into larger, unitized loads, that can be easily handled, moved, and stacked, and that will pack tightly in a ship or yard. Intermodal containers share a number of key construction features to withstand the stresses of intermodal shipping, to facilitate their handling and to allow stacking, as well as being identifiable through their individual, unique ISO 6346 reporting mark.

Transport containers may be transferred between rail, truck, and ship by container cranes at container terminals. Forklifts, reach stackers, straddle carriers, and cranes may be used to load and unload trucks or trains outside of container terminals. Swap bodies, side lifters, tilt deck trucks, and hook trucks may allow transfer to and from trucks with no extra equipment. ISO-standard containers can be handled and lifted in a variety of ways by their corner fixtures, but the structure and strength of forty five-foot (type E) containers limits their tolerance of side-lifting, nor can they be forklifted, based on ISO 3874 (1997).

Transport containers can be transported by container ship, truck and freight trains as part of a single journey without unpacking. Transport containers often include corrugated walls for strength. Each corner of the container may include a twist lock fitting or other fitting for securing the container to other containers and to various transportation devices such as a container trailer for a road-based tractor unit. Reinforcing beams may span the edges of the container, for example the vertical columns that make up the four corners between sidewalls, and the horizontal beams that make up the longitudinal and lateral side edges of the base of the container.

Referring to FIG. 3, an example system 10 is illustrated for injecting and adjusting injection of liquid chemicals into an impacted site 44 for the purpose of remediating the site 44. Two or more two chemical dosing stations 17 may be provided, containing pairs of liquid chemical concentrate components. Liquid chemicals may be supplied to respective control valves 24 via lines 50 and 52, respectively. Each of the two storage reservoir 22 may have associated therewith a chemical suction discharge apparatus 78 and a ball valve 26 located downstream of the chemical suction discharge apparatus 78. A y-strainer 24 may be incorporated to remove any solids that may have precipitated in the chemical storage tank or reservoir 22. A UCS control device (controller) 18 may be used to control the flow of chemicals from a chemical storage tank or reservoir 22. A UCS controller 18 may include a UCS measuring vessel or columnar reservoir 16 that measures the volume of liquid to be passed from the automated valve 26, which may be calculated by one or more sensors included in the UCS controller 18. A pump 36 may be located upstream of a check valve 38.

The device may include a dilution water reservoir 12 that may be connected via a line 46 to a submersible well pump 14. A dilution water reservoir may be used to ensure that water is always available to enable continuous injection if a submersible well pump 14 malfunctions. In remote situations, a submersible well pump 14 may reduce the cost of the process by utilizing ground water already present at the remediation site instead of using a source of water that must be brought to site or otherwise purchased. Water may be fed through a ball valve 26 down a line 48 to mixing station 39. A level transmitter or sensor 20 may be included to measure the volume of water in the water reservoir 12. The chemicals flowing from two or more chemical storage reservoirs 22 may converge with water flowing from the submersible well pump 14 or water reservoir 12 into one mixture that is suitable for injection into the formation.

The lines 58, 60, 62, or 64 may have adequate head pressure for injection. In such an event, a bypass valve 28 may be used via a line 54 to control flow into the injection galleries/group 118 independent of or in tandem with pump 30. Alternatively, in the event that one or more of lines 58, 60, 62, or 64 may not have adequate head pressure, a ball valve 26 located upstream on a line 56 may be opened to supply flow to a y-strainer 24 and a gear pump 30, which may control flow into the various injection galleries 118. A gear pump 30 may be a suitable type of pump for low flow rate distribution. Flow and pressure transducers 32 and 34 may be operated to monitor and adjust flow to the various groups of wells 110. Each line 58, 60, 62, and 64 may have a respective controller 18 and supply valve 26 to adjust or control injection of liquid chemicals into a respective group of one or more wells 110.

Referring to FIG. 3, the use of plural injection galleries or groups (such as groups 66, 68, 70, and 72) may disperse chemical solution via respective injection wells 110 and may use injection sensor wells 112 that form part of a feedback system. Each gallery or group may have a respective manifold, such as manifolds 67, 69, 71, and 73 for groups 66, 68, 70, and 72, respectively. Injection sensor wells 112 may include, but are not limited by, the following sensors: electrical conductivity sensors to evaluate the proxy of remediation by monitoring pH values, temperature sensors to evaluate aerobic conditions which will be present if the bioremediation process is successful, oxygen sensors to evaluate the aerobic conditions of the process, humidity sensors to monitor the moisture of the soil to ensure ion exchange may occur; and carbon dioxide and methane sensors to evaluate the speed of remediation through carbon dioxide and methane production. The present system may be effective in the absence of a feedback system, though without feedback chemicals and flowrate will not be as precise or adaptable to changing conditions or increased knowledge of the site gained from analyzing the sensor data. One or more of the controllers may be incorporated by or controlled by one or more of the other controllers, such as controller 41. Wireless or wired transmission may be used to send control and sensor signals between components.

Referring to FIGS. 1 and 2, the method may be carried out to effect a bioremediation process in situ. An in situ process may be advantageous as such requires less cost than a process that involves disturbing or removing soil. In the example shown, the soil boundaries are established, wells 110 and 112 are drilled and injectors and sensors installed, and the system is operated. Over time, the soil 116 will be remediated, leaving no or only trace amounts of hydrocarbon on site.

Referring to FIG. 11, various soil microbes are known to operate to metabolize and thereby remediate hydrocarbons that contaminate soil 116. There are numerous microorganisms that can degrade hydrocarbons by catalyzing electrons transfer from gasoline to electron acceptors such as oxygen, nitrate, Fe(III) minerals, or sulfate. In some cases, facultative anaerobic bacterial species and facultative aerobic bacterial species are present. The most commonly studied bacteria are from the genus *Pseudomonas*, including *Pseudomonas aeruginosa*, putida, alkaligenes, frateuria, zooglea, azotifigens, azotoformans, chlororaphis, corrugata, extremorientalis, fiavescens, fragi, graminis, japonica, marginalis, migulae, monteilii, mosselii, nitroducens, olveovorans, plecoglossicida, pseudoalcaligenes, psychrophila, stutzeri, taiwanensis, veronii, fulva, and fluorescens. Bacteria from the genus *Bacillus* are also widely studied, including *Bacillus subtlis*, amyloliquefaciens, licheniformis, niacin, pumilis, thurengiensis, cereus, napthovorans, and megaterium. Also commonly studied are bacteria from the genus *Rhodococcus* such as *Rhodococcus zopfii* and rhodochrous and the genus *Arthrobacter* such as *Arthrobacter rseoparaffinus*, petroleophagus, paraffineus, and rubellus and halophilic bacteria such as genus *Halomonas* or *Idiomarina*.

Other bacteria that have been studied are from genera *Methylosinus, Methylomonas, Methylobacterium, Hethylocystics, Alcaligenes, Mycobacterium, Nitrosomonas, Xanthomonas, Spirillum, Vibrio, Bacterium, Achrombacter, Acinetobacter, Flavobacterium, Phenylobacterium, Chromobacterium, Desulfovibrio, Desulfotomaculum, Micrococcus, Sarcina, Streptomyces, Nocardia, Corynebacterium, Arthrobacter, Brevibacterium, Saccharomyces, Stenotrophomonas, Gluconobacter, Agrobacterium, Vibrio, Acinetobacter, and Lactrobacillus*. Exemplary bacterial strains include *Phenylobacterium immobile, Stenotrophomonas maltophilia, Gluconobacter cerinus*, and *Agrobacterium radiobacter*. Ozonophilic bacteria from the genera *Microbacterium, Gordonia, Hydrogenophaga, Nocardia, Spingomonas, Xanthobacteria, Algallgenes, Mycobacteria, Rubrivivax, Arthrobacter, Acidovorax, Burkholderia*, and *Variovarax* have been studied as well as sulfate-reducing bacteria from the genus *Desulfovibrio*, particularly *Desulfovibrio desulfuricans*, and the genus *Desulfotomaculum*. Thermophilic bacteria such as Geobacilli (*Geobacillus midousuji, Geobacillus thermodinitrificans*) have also been studied. Other microbes such as yeasts and fungi have been reviewed in some studies as well as *Ochrobactrum anthropic* and *Ralstonia eutropha*. Other microbes may be present in the soil and may perform a bioremediation process under the appropriate conditions.

The systems 10 and methods disclosed here may be used to remediate a site 44, or to maintain and actively remediate over time. In the latter case, the system 10 may be permanently deployed at an active site, to monitor, target and address any spills or contaminations that occur inadvertently during the life of a site. Although the embodiments here are focused on leveraging native, naturally occurring and/or resident bacteria in the soils, in some cases suitable microbes may be introduced into the soil 116, for example by mixing and injection with or in tandem with the liquid chemicals.

In the claims, the word "comprising" is used in its inclusive sense and does not exclude other elements being present. The indefinite articles "a" and "an" before a claim feature do not exclude more than one of the feature being present. Each one of the individual features described here may be used in one or more embodiments and is not, by virtue only of being described here, to be construed as essential to all embodiments as defined by the claims.

The embodiments of the invention in which an exclusive property or privilege is claimed are defined as follows:

1. A method of long term in situ biogeochemical carbon monitoring of underground soil at a site, the method comprising:
    monitoring, over an extended period, levels of carbon-containing compounds in the underground soil, using plural depletion sensor wells that are arranged within the underground soil below a ground surface at the site and that remain in the underground soil over the extended period, each of the plural depletion sensor wells having a plurality of sensor modules located at two or more isolated depth zones along the depletion sensor well, with the two or more isolated depth zones being separated by bore wall sealing parts between the plurality of sensor modules;
    in which monitoring further comprises using a controller connected to the plural depletion sensor wells, the controller configured to one or more of:
    collect data continuously or at intervals;
    store the data locally; and
    transmit the data;
    in which the underground soil is hydrocarbon contaminated soil;
    in which monitoring comprises monitoring a microbial degradation process by using the plural depletion sensor wells to measure individual levels of each of the following: carbon dioxide, methane, hydrocarbons, and nitrous oxide, in the underground soil; and
    in which monitoring further comprises using a processor to analyze data, from the plural depletion sensor wells and including depth positions of each of the plurality of sensor modules, to determine natural source zone depletion (NSZD) rates of hydrocarbons in the underground soil at the site.

2. The method of claim 1 in which the plurality of sensor modules take continuous or periodic readings over the extended period.

3. The method of claim 1 in which the extended period is a month or longer.

4. The method of claim 3 in which the extended period is a year or longer.

5. The method of claim 1 in which:
    each of the plural depletion sensor wells contains a sensor tubing;
    the plurality of sensor modules each comprise a plurality of sensors, and are on or within the sensor tubing and longitudinally spaced in series along the sensor tubing at different respective longitudinal positions, which correspond to different respective depths of each sensor module below the ground surface.

6. The method of claim 5 in which each sensor module has a housing;
    a sensing part within the housing; and
    a port in the housing putting the sensing part in fluid communication with an exterior of the sensor tubing at the respective longitudinal position of the sensor module.

7. The method of claim 1 in which the plural depletion sensor wells includes:
    depletion sensor wells that are inserted into the hydrocarbon contaminated soil; and
    depletion sensor wells that are inserted into underground soil adjacent to the hydrocarbon contaminated soil.

8. The method of claim 1 further comprising injecting liquid chemicals in situ through a plurality of injection wells into the hydrocarbon contaminated soil, in which the liquid chemicals are selected to biostimulate a microbial degradation process of hydrocarbons to remediate the site.

9. The method of claim 8 in which injecting further comprises controlling the injection of liquid chemicals in situ through the plurality of injection wells in response to signals from the plurality of sensor modules.

10. The method of claim 1 further comprising drilling the plural depletion sensor wells and inserting the plurality of sensor modules therein.

11. The method of claim 1 in which the plural depletion sensor wells are arranged in a network of depletion sensor wells that are arranged at different locations at the site.

12. The method of claim 1 further comprising delivering gas through a tube into one or more of the plural depletion sensor wells.

13. The method of claim 1 in which the bore wall sealing parts each comprise a gasket on exterior surfaces of the plural depletion sensor wells.

14. The method of claim 1 in which the bore wall sealing parts comprise a fluid impermeable barrier or pack between each of the two or more isolated depth zones.

15. The method of claim 14 in which the fluid impermeable barrier or pack comprises bentonite.

* * * * *